US006777180B1

(12) United States Patent
Fisher et al.

(10) Patent No.: US 6,777,180 B1
(45) Date of Patent: Aug. 17, 2004

(54) METHOD FOR FULL-LENGTH CDNA CLONING USING DEGENERATE STEM-LOOP ANNEALING PRIMERS

(75) Inventors: Paul B. Fisher, Scarsdale, NY (US); Dong-Chul Kang, Rutherford, NJ (US)

(73) Assignee: Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/724,028

(22) Filed: Nov. 28, 2000

(51) Int. Cl.[7] .......................... C12Q 1/68; C19P 19/34; C07H 21/02; C07H 21/04; C07H 19/20
(52) U.S. Cl. .................. 435/6; 435/91.2; 435/91.51; 536/23.1; 536/26.74; 536/24.33
(58) Field of Search .................. 435/6, 91.2, 91.5, 435/91.51; 536/23.1, 26.74, 24.33

(56) References Cited

FOREIGN PATENT DOCUMENTS

WO          95/33853    * 12/1995  ............ C12Q/1/68

OTHER PUBLICATIONS

Kang DC, LaFrance R, Su ZZ, Fisher PB (1998). Reciprocal subtraction differential RNA display: an efficient and rapid procedure for isolating differentially expressed gene sequences. Proc Natl Acad Sci USA 10(23):13788–13793.
Hooft van Huijsduijnen R (1998). PCR–assisted cDNA cloning: a guided tour of the minefield. Biotechniques 24(3):390–392.
Lin JJ, Jiang H, Fisher PB (1998). Melanoma differentiation associated gene–9, mda–9, is a human gamma interferon responsive gene. Gene 207(2):105–110.
Carninci P, Nishiyama Y, Westover A, Itoh M, Nagaoka S, Sasaki N, Okazaki Y, Muramatsu M, Hayashizaki Y (1998). Thermostabilization and thermoactivation of the thermolabile enzymes by trehalose and its application for the synthesis of full length cDNA. Proc Natl Acad Sci USA 95(2):520–524.

(List continued on next page.)

*Primary Examiner*—Jeffrey Siew
*Assistant Examiner*—Joyce Tung
(74) *Attorney, Agent, or Firm*—Baker Botts L.L.P.

(57) ABSTRACT

The present invention provides a method for isolating a double-stranded cDNA having a nucleotide sequence of a complete open reading frame which comprises: (A) admixing (i) an isolated single-stranded cDNA, (ii) a first primer capable of forming a stem-loop structure, comprising (a) at the 3' end of the primer, a first random sequence, linked to (b) a second sequence, linked to (c) a third sequence which forms a loop structure, linked to (d) a fourth sequence, at the 5' end of the first primer, which is complementary to the second sequence, under hybridization conditions sufficient for annealing the first sequence of the first primer to the sequence at the 3' end of the single-stranded cDNA, and (iii) a polymerase; (B) incubating the mixture from step (A) under suitable conditions for DNA synthesis; and (C) performing a polymerase chain reaction by admixing (i) an aliquot of the mixture from (B), (ii) a second primer which specifically binds to the single-stranded cDNA, (iii) a third primer which comprises (a) a fifth sequence identical to the third sequence of the first primer, linked to (b) a sixth sequence identical to a portion of the second sequence of the first primer, and (iv) a polymerase, under conditions suitable for a polymerase chain reaction so as to produce a double-stranded cDNA reaction product, thereby isolating the cDNA having the sequence of the complete open reading frame.

9 Claims, 7 Drawing Sheets

OTHER PUBLICATIONS

Anonymous (1996). CapFinder™ PCR cDNA Synthesis Kit. CLONTECHniques 11:2–4.

Carninci P, Kvam C, Kitamura A, Ohsumi T, Okazaki Y, Itoh M, Kamiya M, Shibata K, Sasaki N, Izawa M, Muramatsu M, Hayashizaki Y, Schneider C (1996). High–efficiency full–length cDNA cloning by biotinylated CAP trapper. Genomics 37(3):327–336.

Chenchik A, Diachenko L, Moqadam F, Tarabykin V, Lukyanov S, Siebert PD (1996). Full–length cDNA cloning and determination of mRNA 5' and 3' ends by amplification of adaptor–ligated cDNA. Biotechniques 21(3):526–534.

Su ZZ, Lin J, Shen R, Fisher PE, Goldstein NI, Fisher PB (1996). Surface–epitope masking and expression cloning identifies the human prostate carcinoma tumor antigen gene PCTA–1 a member of the galectin gene family. Proc Natl Acad Sci USA 93(14):7252–7257.

Adams MD, Kerlavage AR, Fleischmann RD, Fuldner RA, Bult CJ, Lee NH, Kirkness EF, Weinstock KG, Gocayne JD, White O, et al. (1995). Initial assessment of human gene diversity and expression patterns based upon 83 million nucleotides of cDNA sequence. Nature 377(6547 Suppl):3–174.

Schaefer BC (1995). Revolutions in rapid amplification of cDNA ends: new strategies for polymerase chain reaction cloning of full–length cDNA ends. Anal Biochem 227(2):255–273.

Bahring S, Sandig V, Lieber A, Strauss M (1994). Mapping of transcriptional start and capping points by a modified 5' RACE technique. Biotechniques 16(5):807–808.

Chencik A, Diachenko L, Chang C, Kuchibhatla S (1994). Great lengths cDNA synthesis kit for high yields of full–length cDNA. CLONTECHniques 9:9–12.

Frohman MA (1994). On beyond classic RACE (rapid amplification of cDNA ends). PCR Methods Appl. 4(1):S40–S58.

Kato S, Sekine S, Oh SW, Kim NS, Umezawa Y, Abe N, Yokoyama–Kobayashi M, Aoki T (1994). Construction of a human full–length cDNA bank. Gene 150(2):243–250.

Kellogg DE, Rybalkin I, Chen S, Mukhamedova N, Vlasik T, Siebert PD, Chenchik A (1994). TaqStart Antibody: "hot start" PCR facilitated by a neutralizing monoclonal antibody directed against Taq DNA polymerase. Biotechniques 16(6):1134–1137.

Maruyama K, Sugano S (1994). Oligo–capping: a simple method to replace the cap structure of eukaryotic mRNAs with oligoribonucleotides. Gene 138(1–2):171–174.

Frohman MA (1993). Rapid amplification of complementary DNA ends for generation of full–length complementary DNAs: thermal RACE. Methods Enzymol 218:340–356.

Fromont–Racine M, Bertrand E, Pictet R, Grange T (1993). A highly sensitive method for mapping the 5' termini of mRNAs. Nucleic Acids Res 21(7):1683–1684.

Hirzmann J, Luo D, Hahnen J, Hobom G (1993). Determination of messenger RNA 5'–ends by reverse transcription of the cap structure. Nucleic Acids Res 21(15):3597–3598.

Jiang H, Fisher PB (1993). Use of a sensitive and efficient subtraction hybridization protocol for the identification of genes differentially regulated during the induction of differentiation in human melanoma cells. Molecular Cellular Differentiation 1:285–299.

Liu X, Gorovsky MA (1993). Mapping the 5' and 3' ends of *Tetrahymena thermophila* mRNAs using RNA ligase mediated amplification of cDNA ends (RLM–RACE). Nucleic Acids Res. 21(21):4954–4960.

Maunders M (1993). DNA and RNA ligases. In: M Burrell (ed.) Methods of Molecular Biology. Enzymes of Molecular Biology. Totowa, NJ: Humana Press 16:213–230.

Rychlik W (1993). Selection of primers for PCR. In: B White (ed.) Methods in Molecular Biology. Totowa, NJ: Humana Press 15:31–40.

Troutt AB, McHeyzer–Williams MG, Pulendran B, Nossal GJ (1992). Ligation–anchored PCR: a simple amplification technique with single –sided specificity. Proc Natl Acad Sci USA 89(20):9823–9825.

Edwards JB, Delort J, Mallet J (1991). Oligodeoxyribonucleotide ligation to single–stranded cDNAs: a new tool for cloning 5' ends of mRNAs and for constructing cDNA libraries by in vitro amplification. Nucleic Acids Res 19(19):5227–5232.

Duyk GM, Kim SW, Myers RM, Cox DR (1990). Exon trapping: a genetic screen to identify candidate transcribed sequences in cloned mammalian genomic DNA. Proc Natl Acad Sci USA 87(22):8995–8999.

Frohman M (1990). RACE: Rapid Amplification of cDNA Ends. In: M Innis, D Gelfand, J Sninsky, T White (eds.), PCR Protocols. San Diego, CA: Academic Press pp. 28–38.

Auch D, Reth M (1990). Exon trap cloning: using PCR to rapidly detect and clone exons from genomic DNA fragments. Nucleic Acids Res. 18(22):6743–6744.

Loh EY, Elliott JF, Cwirla S, Lanier LL, Davis MM (1989). Polymerase chain reaction with single–sided specificity: analysis of T cell receptor delta chain. Science 243(4888):217–220.

Frohman MA, Dush MK, Martin Gr (1988). Rapid production of full–length cDNAs from rare transcripts: amplification using a single gene–specific oligonucleotide primer. Proc. Natl. Acad. Sci. USA 85(23):8998–9002.

D'Alessio JM, Gerard GF (1988). Second–strand cDNA synthesis with *E. coli* DNA polymerase I and RNase H: the fate of information at the mRNA 5' terminus and the effect of *E. coli* DNA ligase. Nucleic Acids Res 16(5):1999–2014.

Kotewicz ML, Sampson CM, D'Alessio JM, Gerard GF (1988). Isolation of cloned Moloney murine leukemia virus reverse transcriptase lacking ribonuclease H activity. Nucleic Acids Res. 16(1):265–277.

Chomczynski P, Sacchi N (1987). Single–step method of RNA isolation by acid guanidinium thiocyanate–phenol–chloroform extraction. Anal Biochem 162(1):156–159.

Wathelet M, Moutschen S, Defilippi P, Cravador A, Collet M, Huez G, Content J (1986). Molecular cloning, full–length sequence and preliminary characterization of a 56–kDa protein induced by human interferons. Eur. J. Biochem 155(1):11–17.

Kornblihtt AR, Umezawa K, Vibe–Pedersen K, Baralle FE (1985). Primary structure of human fibronectin: differential splicing may generate at least 10 polypeptides from a single gene. EMBO J. 4(7):1755–1759.

\* cited by examiner

Figures 1B and 1C
B.
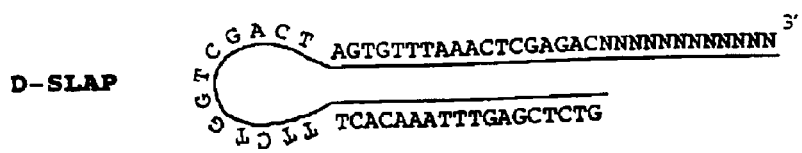
D-SLAP
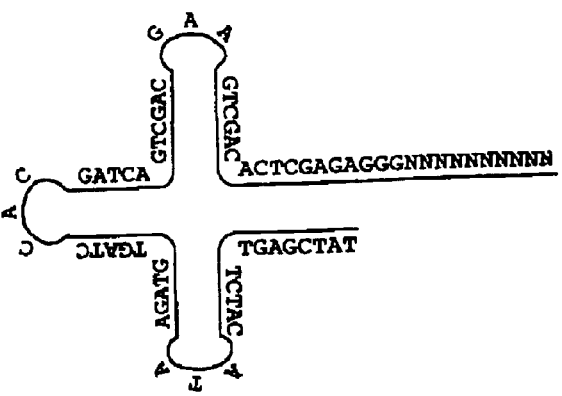
D-CLAP1
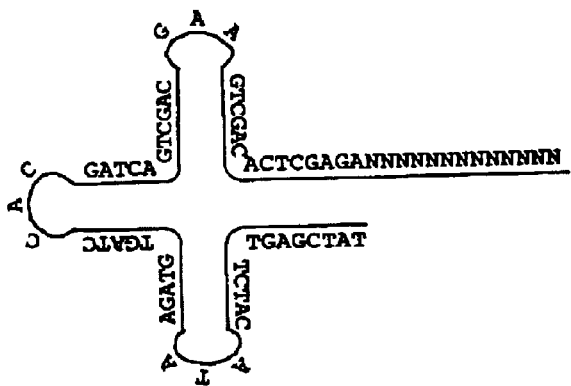
D-CLAP2
C.
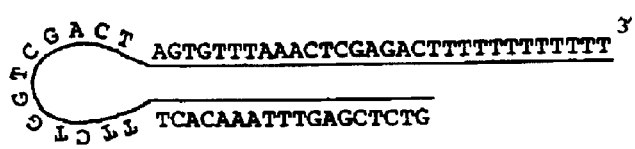
T-SLAP Figures 2A, 2B, and 2C
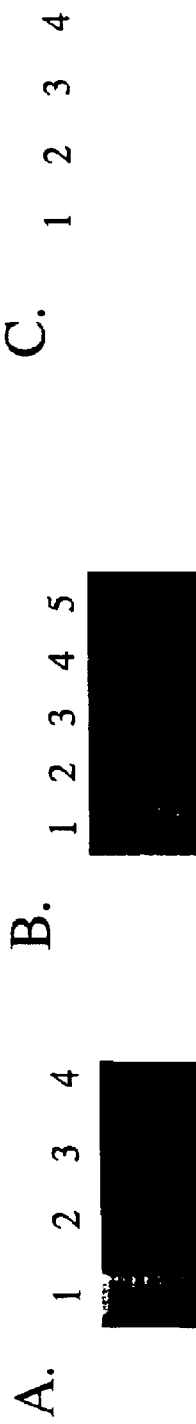

D.

Lane 1- ctl with EST
Lane 2- IFN-ß with EST
Lane 3- ctl with C-ORF product
Lane 4- IFN-ß with C-ORF product

E.

Lane 1- 1 kb ladder
Lane 2- RT-PCR R2/S8
Lane 3- RT-PCR R4/S8

Lane 1 & 6- 1 kb ladder
Lane 2- mda-9
Lane 3- fibronectin
Lane 4- PCTA-1 (R1)
Lane 5- PCTA-1 (pA)
Lane 7- mda-5
Lane 8- ISG-56

Lane 1- 1 kb ladder
Lane 2- fibronectin
Lane 3- PCTA-1 (pA)
Lane 4- mda-9
Lane 5- ISG 56

Lane 1- 1 kb ladder
Lane 2- AP only
Lane 3- GSP/AP
Lane 4- GSP only

METHOD FOR FULL-LENGTH CDNA CLONING USING DEGENERATE STEM-LOOP ANNEALING PRIMERS

The invention disclosed herein was made with Government support under Grant Nos. CA74468 and NS31492 from the U.S. Department of Health and Human Services, National Institutes of Health. Accordingly, the U.S. Government has certain rights in this invention.

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

BACKGROUND OF THE INVENTION

The human genome is estimated to contain 100,000 genes, the expressions of which define the functionality of a cell (1). Current technological advances, including large-scale DNA sequencing, efficient library construction and manipulation and PCR-based gene expression monitoring, have resulted in the identification of more than 87,000 unique expression sequence tags (ESTs) in diverse cell types and under various physiological conditions (1). Approximately 12% of the ESTs have significant homology with previously identified genes and the remainder require further investigation to define their identity and biological relevance (1). However, ESTs, short stretches of expressed genes, can only provide limited information as to the identity and biological role of specific genes. A more thorough analysis of the ESTs requires a determination of the full protein coding sequences for these expressed genes.

Several approaches are routinely used to obtain cDNAs containing protein-encoding sequences from ESTs. These include, library screening (2) and the PCR-based rapid amplification of cDNA ends (RACE) strategy (3). A less frequently employed scheme, exon trapping is also amendable to cDNA cloning from genomic fragments (4,5).

A number of cDNA libraries from diverse sources are commercially available. This can in specific instances reduce the burden of producing cDNA libraries that are required for screening for cDNAs. However, even with well-constructed cDNA libraries, several rounds of screening and verification are often required to obtain even a single complete cDNA (2). This process is laborious and can require months of intensive effort. What exacerbates the situation is that cDNA library screening occasionally results in incomplete cDNAs lacking full protein coding information. This occurs primarily because of premature termination of reverse transcription and the self-priming procedure during second strand cDNA synthesis (2, 6, 7). Additionally, obtaining cDNA of low abundance mRNA is rarely achievable unless the cDNA library is high titer and minimally amplified (2). In these contexts, the current approach of cDNA library screening to obtain full protein coding sequence is often costly, laborious and inefficient.

SUMMARY OF THE INVENTION

The present invention provides a method for isolating a double-stranded cDNA having a nucleotide sequence of a complete open reading frame which comprises: (A) admixing (i) an isolated single-stranded cDNA, (ii) a first primer capable of forming a stem-loop structure, comprising (a) at the 3' end of the primer, a first random sequence, linked to (b) a second sequence, linked to (c) a third sequence which forms a loop structure, linked to (d) a fourth sequence, at the 5' end of the first primer, which is complementary to the second sequence, under hybridization conditions sufficient for annealing the first sequence of the first primer to the sequence at the 3' end of the single-stranded cDNA, and (iii) a polymerase; (B) incubating the mixture from step (A) under suitable conditions for DNA synthesis; and (C) performing a polymerase chain reaction by admixing (i) an aliquot of the mixture from (B), (ii) a second primer which specifically binds to the single-stranded cDNA, (iii) a third primer which comprises (a) a fifth sequence identical to the third sequence of the first primer, linked to (b) a sixth sequence identical to a portion of the second sequence of the first primer, and (iv) a polymerase, under conditions suitable for a polymerase chain reaction so as to produce a double-stranded cDNA reaction product, thereby isolating the cDNA having the sequence of the complete open reading frame.

BRIEF DESCRIPTION OF THE FIGURES

FIGS. 1A–C. Schematic of the C-ORF procedure and the primers used in this approach. FIG. 1A. In C-ORF, specifically designed primers anneal to the 3' end of the first strand cDNA. Extended cDNA from this primer can be amplified by PCR with a gene specific primer (GSP) and a universal anchor primer containing the annealing primer sequence. This method dispenses with rate limiting steps of conventional RACE, such as homopolymer tailing or single strand ligation. FIG. 1B. Primers (D-SLAP, D-CLAP1 and D-CLAP2) used in the 5' C-ORF reaction. The stem-and-loop structure of these primers is designed to prevent, by steric hindrance, degenerate regions from annealing to internal sites, thereby insuring efficient extension of the gene product. D-CLAP1 contains additional GGG sequences to enhance annealing to the C-homopolymer tail generated by the TdT-like activity of reverse transcriptase (RT). FIG 1C. In the T-SLAP reagent, dT replaces the random sequences used for the reverse transcription reaction as a primer.

FIGS. 2A–2E. C-ORF cloning of the novel gene mda-5. FIG. 2A. Mda-5 C-ORF products (12 µl nested PCR) with reverse transcription reactions at specified temperature are resolved in a 1% agarose gel containing EtBr. FIG. 2B. C-ORF products of mda-5 performed with different amounts of the D-SLAP reagent and the anchor primer in primary PCR for second strand cDNA synthesis. FIG. 2C. An autoradiogram of Southern blot hybridization of C-ORF products of mda-5 resolved in (B) with $^{32}$P-labeled nested primers. FIG. 2D. An autoradiogram of Northern blot hybridization of RNA samples prepared from HO-1 human melanoma cells either left alone (Con) or treated with 2,000 U/ml IFN-β plus 10 ng/ml mezerein. Left panel was probed with $^{32}$P-labeled mda-5 EST (0.4 kb) previously cloned by library screening. The right panel was probed with a $^{32}$P-labeled 1.8-kb mda-5 C-ORF product. FIG. 2E. RT-PCR analysis using sequence information derived from the mda-5 C-ORF product. RT-PCR was performed using 2 µl of the reverse transcription reaction with the specified primer, either R2S8 or R4S8, and 12 µl of the reaction was run on the gel.

FIG. 4A. C-ORF products obtained using the D-CLAP1 reagent for the specified genes were separated in a 1% agarose gel. Authentic bands of the appropriate target size are marked with dots. Duration of extension in PCR was 3 min for mda-9 and ISG-56, and 8 min. For PCTA-1 (pA) and fibronectin. FIG. 4B. C-ORF products obtained using the D-CLAP2 reagent for the specified genes were separated in 1% agarsoe gel. Authentic bands of the correct target size are marked with arrows. The duration of extension in PCR was 3 min for mda-9 and ISG-56, 6 min for mda-5 and 8 min for PCTA-1 and fibronectin.

DETAILED DESCRIPTION OF THE INVENTION

Figure 1A:
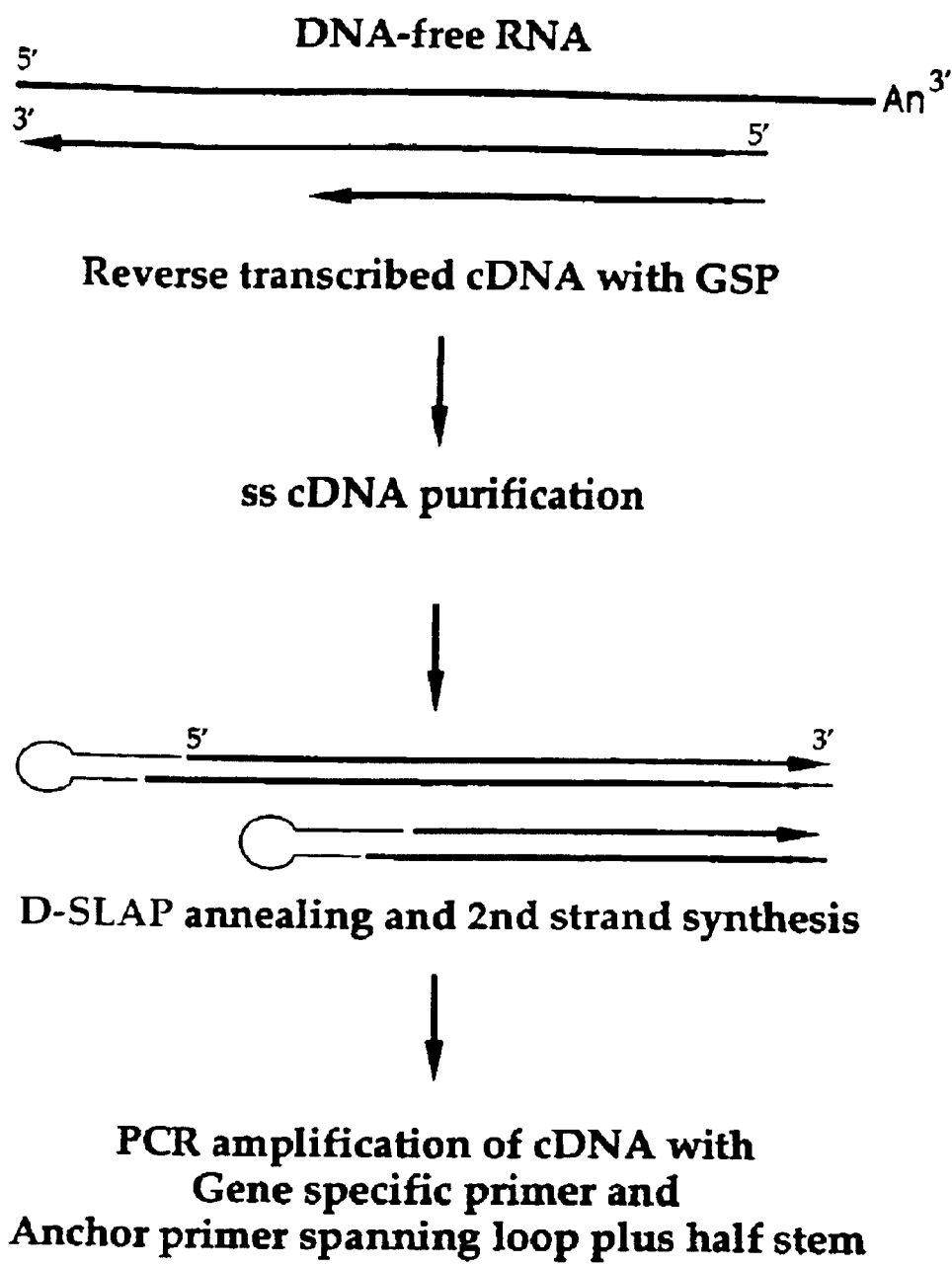

The present invention provides for a method for isolating a double-stranded cDNA having a nucleotide sequence of a complete open reading frame which comprises: A) admixing (i) an isolated single-stranded cDNA, (ii) a first primer capable of forming a stem-loop structure, comprising (a) at the 3' end of the primer, a first random sequence, linked to (b) a second sequence, linked to (c) a third sequence which forms a loop structure, linked to (d) a fourth sequence, at the 5' end of the first primer, which is complementary to the second sequence, under hybridization conditions sufficient for annealing the first sequence of the first primer to the sequence at the 3' end of the single-stranded cDNA, and (iii) a polymerase; B) incubating the mixture from step (A) under suitable conditions for DNA synthesis; and C) performing a polymerase chain reaction by admixing (i) an aliquot of the mixture from (B), (ii) a second primer which specifically binds to the single-stranded cDNA, (iii) a third primer which comprises (a) a fifth sequence identical to the third sequence of the first primer, linked to (b) a sixth sequence identical to a portion of the second sequence of the first primer, and (iv) a polymerase under conditions suitable for a polymerase chain reaction so as to produce a double-stranded cDNA reaction product, thereby isolating the cDNA having the sequence of the complete open reading frame.

In one embodiment of the invention, the single-stranded DNA is a 5' portion of a cDNA reverse transcribed from an mRNA. t In another embodiment of the invention, the first primer has the sequence 3'-NNNNNNNNNNNNNCAGAGCTCA-AATTTGTGATCAGCTGGTCTTTCACAAATTTGAGC-TCTG-5' (D-SLAP; SEQ ID NO:30).

In another embodiment of the invention, the first primer has the sequence 3'-NNNNNNNNNNGGGAGAGCTCA-CAGCTGAAGCAGCTGACTAGCACCTAGTGTAGAA-TACATCTTGAGCTAT-5' (D-CLAP1; SEQ ID NO:31).

In a further embodiment of the invention, the first primer has the sequence 3'-NNNNNNNNNNNNNAGAGCTCA-CAGCTGAAGCAGCTGACTAGCACCTAGTGTAGA-ATACATCTTGAGCTAT-5' (D-CLAP2; SEQ ID NO:32).

In another embodiment of the invention, the first primer comprises an inosine nucleotide.

In a further embodiment of the invention, the loop structure is a simple loop structure, or a cloverleaf loop structure.

The present invention provides for a method for generating a cDNA library which comprises: A) admixing (i) a population of single-stranded cDNA molecules which were reverse transcribed with an oligo-dT sequence linked to a defined nucleotide sequence, (ii) a first primer capable of forming a stem-loop structure, comprising (a) at the 3' end of the primer, a first random sequence linked to (b) a second sequence, linked to (c) a third sequence which forms a loop structure, linked to (d) a fourth sequence, at the 5' end of the first primer, which is complementary to the second sequence, under hybridization conditions sufficient for annealing the first sequence of the first primer to the sequence at the 3' end of the single-stranded cDNA, and (iii) a polymerase; B) incubating the mixture from step (A) under suitable conditions for DNA synthesis by the polymerase; and C) performing a polymerase chain reaction by admixing (i) an aliquot of the mixture from (B), (ii) a second primer which has the identical sequence as the defined nucleotide sequence of the primer in (A) (i), (iii) a third primer which comprises (a) a fifth sequence identical to the third sequence of the first primer, linked to (b) a sixth sequence identical to a portion of the second sequence of the first primer, and (iv) a polymerase under conditions suitable for a polymerase chain reaction so as to produce double-stranded cDNA reaction products thereby generating a cDNA library.

In one embodiment, Xhe single-stranded DNA is a cDNA reverse transcribed from an mRNA.

In another embodiment of the invention, the first primer has the sequence 3'-NNNNNNNNNNNNNCAGAGCTCA-AATTTGTGATCAGCTGGTCTTTCACAAATTTGAGC-TCTG-5' (D-SLAP; SEQ ID NO:30).

In another embodiment of the invention, the first primer has the sequence 3'-NNNNNNNNNGGGAGAGCTCACA-GCTGAAGCAGCTGACTAGCACCTAGTGTAGAAT-ACATCTTGAGCTAT-5' (D-CLAP1; SEQ ID NO:31).

In another embodiment of the invention, the first primer has the sequence 3'-NAGAGCTCACAGCTGAAGCAG-CTGACTAGCACCTAGTGTAGAATACATCTTGAGCT-AT-5' (D-CLAP2; SEQ ID NO:32).

In another embodiment of the invention, the first primer comprises an inosine nucleotide.

In another embodiment of the invention, the loop structure is a simple loop structure, or a cloverleaf loop structure.

The present invention provides for a kit for the generation of a complete open reading frame double-stranded cDNA of interest which comprises: (i) a first primer capable of forming a stem-loop structure, comprising (a) at the 3' end of the primer, a first random sequence linked to (b) a second sequence, linked to (c) a third sequence which forms a loop structure, linked to (d) a fourth sequence, at the 5' end of the first primer, which is complementary to the second sequence, and (ii) a second primer which comprises (a) a fifth sequence identical to the third sequence of the first primer, linked to (b) a sixth sequence identical to a portion of the second sequence of the first primer.

The present invention also provides for a method for isolating a double-stranded cDNA having a nucleotide sequence of a complete open reading frame which comprises: (a) admixing (i) a biological sample containing mRNA, (ii) a primer which forms a stem-loop structure, comprising: (a) a poly-T sequence at the 3' end of the primer linked to (b) a first random sequence linked to (c) a second sequence which forms a loop structure linked to (d) a third sequence at the 5' end of the primer which is complementary to the first sequence, and (iii) a reverse transcriptase, under hybridization conditions sufficient for annealing the primer to the mRNA poly-A sequence; (b) incubating the mixture from step (a) under suitable conditions for reverse transcription; (c) performing a polymerase chain reaction with an aliquot of the mixture from step (b) using one gene-specific primer which is pre-defined and one primer which has a sequence identical to at least a portion of the primer sequence of element (ii), thereby isolating the cDNA having the sequence of the complete open reading frame.

In one embodiment of the invention, the primer has the sequence 3'-TTTTTTTTTTTCAGAGCTCAAATTTGT-GATCAGCTGGTCTTTCACAAATTTGAGCTCTG-5' (T-SLAP; SEQ ID NO:33).

In addition, the present invention is directed to a method for isolating a double-stranded cDNA having a nucleotide sequence of a complete open reading frame which comprises: A) admixing (i) an isolated single-stranded cDNA, (ii) a first primer capable of forming a stem-loop structure, comprising (a) at the 3' end of the primer, a first random sequence, linked to (b) a second sequence, linked to (c) a third sequence which forms a loop structure, linked to (d) a fourth sequence, at the 5' end of the first primer, which is complementary to the second sequence, under ligation conditions sufficient for ligating the first sequence of the first primer to the sequence at the 3' end of the single-stranded cDNA, and (iii) a ligase; B) incubating the mixture from step (A) under suitable conditions for ligation; and C) performing a polymerase chain reaction by admixing (i) an aliquot of the mixture from (B), (ii) a second primer which specifically binds to the single-stranded cDNA, (iii) a third primer which comprises (a) a fifth sequence identical to the third sequence of the first primer, linked to (b) a sixth sequence identical to a portion of the second sequence of the first primer, and (iv) a polymerase under conditions suitable for a polymerase chain reaction so as to produce a double-stranded cDNA reaction product, thereby isolating the cDNA having the sequence of the complete open reading frame.

The present invention provides for a method for generating a cDNA library which comprises: A) admixing (i) a population of single-stranded cDNA molecules which were reverse transcribed with an oligo-dT sequence linked to a defined nucleotide sequence, (ii) a first primer capable of forming a stem-loop structure, comprising (a) at the 3' end of the primer, a first random sequence linked to (b) a second sequence, linked to (c) a third sequence which forms a loop structure, linked to (d) a fourth sequence, at the 5' end of the first primer, which is complementary to the second sequence, under ligation conditions sufficient for ligation of the first sequence of the first primer to the sequence at the 3' end of the single-stranded cDNA, and (iii) a ligase; B) incubating the mixture from step (A) under suitable conditions for DNA synthesis by the polymerase; and C) performing a polymerase chain reaction by admixing (i) an aliquot of the mixture from (B), (ii) a second primer which has the identical sequence as the defined nucleotide sequence of the primer in (A) (i), (iii) a third primer which comprises (a) a fifth sequence identical to the third sequence of the first primer, linked to (b) a sixth sequence identical to a portion of the second sequence of the first primer, and (iv) a polymerase under conditions suitable for a polymerase chain reaction so as to produce double-stranded cDNA reaction products thereby generating a cDNA library.

The following are several applications of the present invention:
1. Cloning the 5' end of a cDNA from an EST.
2. Cloning the 3' end of a cDNA from an EST by performing C-ORF in a reverse transcription reaction.
3. Construction of a cDNA library containing a high proportion of full-length cDNAs.
4. Genomic cloning, both upstream and downstream regions of known sequences.
5. Capture nucleic acid of specific sequence for purification and diagnostic purposes.
6. Gene inactivation by inhibiting mRNA entry onto the ribosome for translation.
7. Cloning family of genes, such as kinases.
8. Mutational analysis.
9. Chromosomal mapping.

One advantage of the present invention is that the stem-loop degenerate primer used herein preferentially anneals to single-strand cDNA and permits PCR amplification. This method overcomes the low efficiency of TdT reaction of 5' RACE method and linker ligation by RNA ligase. The present invention provides the advantage of permitting single step isolation of large cDNAs. The limit for 5' RACE is approximately<1 kbases. The methods presented herein allow for reproducible and efficient isolation of full-length cDNAs from partial cDNAs such as ESTs and other partial clones.

Multiple approaches have been developed for isolating differentially expressed gene sequences, including differential RNA display (DD), reciprocal subtraction differential RNA display (RSDD), representational difference analysis (RDA), serial analysis of gene expression (SAGE) and subtraction hybridization. These methodologies result predominantly in partial cDNAs or relatively short gene sequences representing expressed sequence tags (ESTs). In order to gain insights into the putative function of specific genes it is often necessary to clone a full-length cDNA. Current procedures for achieving this goal are time consuming, inefficient and sometimes quite formidable. Currently, the most frequently used strategies for full-length cDNA isolation involve screening of 5' stretch cDNA libraries and/or the PCR-based 5' RACE approach. Screening cDNA libraries is very labor intensive and often yields incomplete cDNA, which necessitates the use of additional 5' cloning methods such as 5' RACE. To reach the 5' end of a cDNA two PCR-based methods have been used, 5' RACE employing terminal deoxytransferase to prime the 3' end of the first strand cDNA and linker ligation using RNA ligase. However, these methods are limited in effectiveness because of the low efficiency of the priming procedure. We describe a novel way of priming the 3' end of first strand cDNA that allows the second strand of cDNA to be synthesized preferentially from the 3' end of the first strand of cDNA.

Degenerate stem and loop cDNA end annealing primer (D-SLAP) methods were designed to preferentially anneal to the 3' end of the first strand of cDNA. The primer consists of two functional components: 1) a stem and a loop (stem-and-loop) component and 2) the annealing of degenerate nucleotides. The stem-and-loop structure sterically hinders degenerate oligonucleotides from annealing to the middle of a cDNA and promotes preferential anealing to the end of the first strand of cDNA. Conceptually, the stem-and-loop of the D-SLAP method should form molecular complexes at higher temperatures preventing the binding of degenerate oligonucleotides. This could occur because the longer region of potential base pairing in the stem-and-loop region should facilitate intramolecular annealing over degenerate oligonucleotide binding. Alternatively, the longer region of base pairing in the stem-and-loop and the intramolecular annealing reaction mechanics may facilitate formation of stem-and-loop structure prior to degenerate oligonucleotide annealing.

Full-length cloning of a 5' sequence of cDNA using the D-SLAP method was performed as follows. Total RNA (2 μg) treated with RNase-free DNase was extracted and reverse transcribed with a gene specific primer using MMLV RT (Superscript RT II from Gibco-BRL) as in the 5' RACE protocol (Gibco-BRL) at 48° C. and inactivated by incubation at 85° C. for 5 minutes. After treatment with a mixture of RNase H and RNase I for 30 minutes at 37° C., first strand cDNA was purified with GlassMax® (Gibco-BRL) and the second strand of cDNA was synthesized using D-SLAP method. Purified first strand cDNA was mixed with 1 pmole of D-SLAP reactants and KlenTaq reaction buffer, and heated at 95° C. for 1.5 minutes and slowly cooled down to 45° C. KlenTaq (0.25 μl, Clontech) and dNTP (0.5 μl of 10 mM, Gibco-BRL) were added to the 45° C. equilibrated reaction mixture and subsequently second strand cDNA synthesis was performed by incubation at 68° C. for 30 minutes. A PCR reaction was set up with 5 μl of the cDNA synthesis reaction mixture, 5' anchor primer designed from the loop area of D-SLAP and a gene specific primer. Secondary PCR was performed with 0.5 μl of the primary PCR product, the same 5' anchor primer (for nested PCR primers) and a nested gene specific primer.

D-SLAP second strand synthesis was applied to clone a full-length mda-5 (melanoma differentiation associated gene-5) cDNA. This approach reproducibly yielded an approximately ~2 Kb mda-5 amplification product. The DNA fragment was isolated and confirmed to be mda-5 by Northern blot analysis and sequencing. This experiment result represents proof-of-practice for the D-SLAP method. One improvement of this procedure includes using inosine nucleotide-containing degenerate primers and incorporating a single tube second strand synthesis and PCR amplification procedure. If successful these modifications will significantly simplify full-length cDNA cloning using the D-SLAP methodology. Additionally, the D-SLAP method can be used to generate cDNA libraries for second strand synthesis that contain a high proportion of full-length cDNAs. Moreover, with tub modification of the D-SLAP procedure can be used to clone the 3' end of a partial cDNA by substituting oligo dT for the degenerate primers and incorporating a reverse transcription reaction.

The D-SLAP method can also be formatted for use as a kit for the generation of full-length cDNAs. It will have wide applicability for the efficient and rapid production of full-length cDNAs from ESTs. In these contexts, this approach represents a major scientific advance in gene cloning with significant financial potential.

The present invention provides for novel molecular approaches for the identification of genes and gene products amenable for the targeted therapy of human diseases. In addition, there is specific focus on autoimmune dieseases, cancer, cardiovascular and infectious disease states.

One purpose of the present invention is to provide novel technoogies for the identification, complete open reading frame cDNA cloning and functional analysis of genes relevant to human diseases. In addition, the present invention also utilizes molecular approaches and high throughput screening procedures to identify small molecules and novel gene products that can directly intervene in disease processes.

The present invention provides for efficient production of the complete open reading frames of cDNAs from partial cDNAs and ESTs. This approach is called the Complete Open Reading Frame (C-ORF) cloning method. This method also offers the ability to generate cDNA libraries which contain a high proportion of full-length cDNAs. A modification of this method is wherein a 3' C-ORF which permits cloning of complete open reading frame cDNAs from partial internal cDNAs missing 3' regions.

This invention also provides for functional gene evaluation. This includes the efficient and stable generation of target cells containing inducible genes for direct functional analysis and the identification of down-stream target genes and biochemical pathways mediating biological responses. These methods include the use of promoters to drive inducible target genes that are more resistant to loss of gene expression after integration and vector constructs that induce tight-regulation of target gene expression.

In addition, this invention also provides for promoter generation and analysis methods which will permit the rapid identification of the promoter region of potentially important genes regulating disease states. The promoters are used as part of a small molecule screening effort, the Rapid Promoter Screening (RPS) approach, to identify potential inhibitors and activators of disease gene transcription. These small molecules will be tested for efficacy in ameliorating specific disease states.

The practice of the present invention will employ, unless otherwise indicated, conventional techniques of molecular biology, microbiology and recombinant DNA technology which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extra-chromosomal plasmids. This stability is demonstrated by the ability of the eucaryotic cell to establish cell lines or clones comprised of a population of daughter cells containing the exogenous DNA.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM $MgCl_2$, 6 MMDTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, re-ligation can be prevented in vectors which have been double digested by additional restriction enzyme digestion of the unwanted fragments.

The Complete Open Reading Frame (C-ORF) Technology: A Simple and Efficient Approach for Obtaining the Entire Protein Codina Region of Genes The ability to analyze a gene's function often requires the identification of the protein-coding region of that gene. Although a number of approaches, including library screening and rapid amplification of cDNA ends (RACE), have been used extensively to identify the complete open reading frame. (ORF) of specific cDNA's, these approaches can be inefficient, time consuming and costly. An approach is described, the C-ORF (complete open reading frame) technology, that results in the rapid and efficient identification of protein coding regions of genes in which limited sequence information is available. This scheme was applied successfully, in the majority of cases involving only a single application, in identifying and cloning the complete ORF of genes ranging in size from 1.2 to 8 kb. The C-ORF approach will prove valuable in efforts designed to define the function of a gene in situations where only expressed sequence tags (ESTs) or incomplete cDNA genetic information is available. This strategy offers promise for accelerating the pace of gene discovery and for rapidly advancing the fields of functional genomics, proteomics and pharmacogenomics.

The human genome is estimated to contain 100,000 genes, the expressions of which define the functionality of a cell (1). Current technological advances, including large-scale DNA sequencing, efficient library construction and manipulation and PCR-based gene expression monitoring, have resulted in the identification of more than 87,000 unique expression sequence tags (ESTs) in diverse cell types and under various physiological conditions (1). Approximately 12% of the ESTs have significant homology with previously identified genes and the remainder require further investigation to define their identity and biological relevance (1). However, ESTs, short stretches of expressed genes, can only provide limited information as to the identity and biological role of specific genes. A more thorough analysis of the ESTs requires a determination of the full protein coding sequences for these expressed genes.

Several approaches are routinely used to obtain cDNAs containing protein-encoding sequences from ESTs. These include, library screening (2) and the PCR-based rapid amplification of cDNA ends (RACE) strategy (3). A less frequently employed scheme, exon trapping is also amendable to cDNA cloning from genomic fragments (4,5).

A number of cDNA libraries from diverse sources are commercially available. This can in specific instances reduce the burden of producing cDNA libraries that are required for screening for cDNAs. However, even with well-constructed cDNA libraries, several rounds of screening and verification are often required to obtain even a single complete cDNA (2). This process is laborious and can require months of intensive effort. What exacerbates the situation is that cDNA library screening occasionally results in incomplete cDNAs lacking full protein coding information. This occurs primarily because of premature termination of reverse transcription and the self-priming procedure during second strand cDNA synthesis (2, 6, 7). Additionally, obtaining cDNA of low abundance mRNA is rarely achievable unless the cDNA library is high titer and minimally amplified (2). In these contexts, the current approach of cDNA library screening to obtain full protein coding sequence is often costly, laborious and inefficient.

Recent improvements in cDNA library construction can significantly increase the proportion of full-length cDNAs. These approaches include trapping $m^7GTP$-cap in RNA-DNA hybrid (8), ligation of oligonucleotides to de-capped mRNA with T4 RNA ligase (9) and Cap-switch cDNA Library Synthesis Kit utilizing the terminal deoxyribonucleotide transferase (TdT)-like activity of reverse transcriptase (10–12). However, some of these newer protocols involve additional steps including cumbersome chemical or enzymatic reactions (8, 9). Although cDNA library screening can identify mRNA variants and provide more reliable sequence information than PCR, the construction of high-quality cDNA libraries is not routinely achievable in most research laboratories (13). Considering the cost of cDNA library construction, clonal redundancy, the laborious nature of the subsequent screening approach and the cost of sequencing, improved approaches for obtaining full-length cDNAs and complete open reading frames for cDNAs are required.

PCR-based cDNA cloning methods such as RACE and variations of this scheme have certain advantages over cDNA library screening approaches (14). Since Frohman et al. (15) introduced the RACE approach, this method has been modified extensively (14). Fundamentally, RACE employs a single-side specific PCR of a target cDNA synthesized by reverse transcription with a gene specific primer. The second universal primer site is provided by homopolymer-tailing with Tdt (15,16) or by single strand anchor ligation to the first strand cDNA with T4 RNA ligase (17,18). PCR is. performed with the gene specific primer and a universal primer, and the products are purified and analyzed. In. addition to 5' cDNA end cloning and analysis, ligation of oligonucleotide to 3' mRNAs (19) or reverse transcription with an oligo-dT-anchor hybrid primer (15) also enables 3' end cloning of mRNAs. The entire procedure requires two days, which represents a significant reduction in time in comparison with cDNA library screening. Moreover, the amplification power of PCR permits the cloning of low abundant mRNA molecules and requires relatively small amounts (1 µg of total RNA) of starting material (20).

The application of RACE for obtaining full-length cDNAs, however, is not as simple and straightforward as the theory behind the technique suggests. Problems, such as premature termination of reverse transcription because of the secondary structure of the mRNA, is common to both RACE and cDNA library construction (6). Thermostable RT (14) or the addition of threhalose (21) permits reverse transcription at higher temperatures (~50 to 60° C.) and can reduce secondary structure formation. PCR-related problems encountered using the various RACE procedures include:
1. Generation of non-specific products due to the insufficient specificity and priming of the universal primer to intragenic sites.
2. A high rate of false incorporation of bases frequently occurs using Taq polymerase, a problem which can be reduced (3-to-5-fold), but not completely eliminated, by using enzymes with proofreading activity.
3. Amplification biases often resulting in the preferential amplification of shorter products (less than 1 kb).
4. Production of artifacts by amplification of incorrect hybrid molecules resulting from template self-annealing or mispriming (13, 20).

Thus, amplification of shorter fragments than target length probably arises from premature termination of reverse transcription, intragenic priming by universal primers, and/or the denaturation and annealing kinetics of PCR reactions (22). Consequently, application of the RACE approach for producing complete protein coding sequence of long messages require successive rounds of this procedure, which obviates the time and laborsaving features of this method.

A rate limiting step in the RACE process is the generation of a second universal primer site by an enzymatic reaction of TdT or T4 RNA ligase. However, not only is the TdT reaction inefficient, but also the length of homopolymer tails added by TdT is difficult to control, resulting in heterogeneous PCR products that are troublesome to sequence (13, 15, 18, 23). T4 RNA ligase is also inefficient, especially with longer substrates, and it requires a high concentration of substrate because of its high $K_m$ (millimolar) (24). Furthermore, donor oligonucleotides need to be phosphorylated at their 5' end and deoxygenated at their 3' end to avoid ligation to the 5' end of the first strand cDNA (17, 18). In addition to these technical difficulties associated with RACE approaches, in many cases it is often necessary to repeat this process numerous times to obtain a full protein coding sequence (13).

To overcome the problem of fragmented cloning and inefficient second strand cDNA priming, procedures have been described that employ PCR-selection of fully transcribed cDNA by ligation of defined oligo ribonucleotides to the de-capped mRNA 5' end (RLM-PCR) or a double-strand adapter ligation protocol (19, 23, 25, 26). Although these methods significantly increase the yield of full-length cDNA clones, the procedures require complicated and technically challenging chemical procedures such as i-elimination (19) and enzymatic reactions (bacterial alkaline phosphatase and tobacco acid pyrophosphatase) and they are not always successful.

Cloning protein-coding sequences from ESTs is a prerequisite, but often a rate-limiting step, in studying the biological effects of a given DNA moiety. With current technologies and the abundance of information present in genebank databases, cDNA cloning is not as formidable a task as it once was. However, currently available methods are not readily amenable to most cloning projects since they are costly, require a series of complicated enzyme reactions and involve extensive cDNA library screenings. Development of an improved approach capable of reliably yielding protein coding information without requiring repetitive applications, would save both cost, labor and time over current RACE and cDNA library screening protocols.

We now describe a method for rapidly amplifying cDNAs' C-ORF, which significantly simplifies and improves upon current strategies for obtaining a complete open reading frame for protein encoded by ESTs or incomplete cDNAs. Instead of generating a universal primer site with TdT-tailing or anchor ligation, a degenerate stem and loop annealing primer (D-SLAP) or a degenerate clover-leaf annealing primer (D-CLAP) which anneals to the 3' end of the first strand cDNA provides a universal primer site for second strand cDNA provides a universal primer site for second strand cDNA synthesis and subsequent PCR. The C-ORF protocol includes reverse transcription, second strand cDNA synthesis and PCR amplification with nested primers and requires RT, Taq polymerase and the D-SLAP reagent. Proof-of-principle for the C-ORF technology has come from an analysis of both known and novel gene sequences resulting in the identification of complete open reading frames for cDNAs ranging in size from 1.2 to 8 kb. These include the following known genes, interferon stimulated gene-56 (ISG-56; 1.5 kb) (27), melanoma differentiation associated gene-9 (mda-9; 2 kb) (28), prostate carcinoma tumor antigen gene-1 (PCTA-1; 3.5 and 6 kb) (29) and fibronectin (8 kb) (30). Complete open reading frames for novel cDNAs identified by C-ORF include, melanoma differentiation associated gene-5 (mda-5; 3.5 kb) (31, 32), progression elevated gene-28 (PEGen 28; 1.2 kb) (33), progression elevated gene-42 (PEGen 42; 1.2 kb) (33), progression suppressed gene-12 (PSGen 12; 1.2 kb) (33) and a novel gene associated with differentiation and senescence (OLD-35; 2 kb) (34). In addition, the C-ORF technology can also be used for determining complete 3' sequence information. Using oligo dT-SLAP in a reverse transcription reaction allowed 3' end cloning of PCTA-1 (1 kb fragment (29), PEGen 28 (0.7 kb fragment) (33) and OLD-35 (34). Prerequisites for the C-ORF protocol include at least 100-bp of sequence information, the approximate size of the cDNA and RNA from an appropriate target cell. Based on the effectiveness, simplicity, rapidity and labor- and cost-efficiency of the C-ORF procedure, this methodology can accomplish both single and multiple cDNA cloning projects simultaneously. In the context, C-ORF will be of inestimable value to genomic, proteomic and pharmacogenomic research efforts directed toward defining the functional roles for ESTs and partial cDNAs.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1: The Complete Open Reading Frame (C-ORF) Technology: A Simple and Efficient Approach for Obtaining the Entire Protein Coding Region of Genes Materials and Methods Cell cultures: HO-1 human melanoma cells (32) were grown in DMEM supplemented with 10% fetal bovine serum, 100 U/ml penicillin G and 100 $\mu$g/ml streptomycin in a 5% $CO_2$ 95% air humidified incubator at 37° C. Du-145, a human prostate carcinoma cell line, was cultured in RPMI supplemented with the same reagents. Cells were maintained in the logarithmic phase of growth by subculturing 1:10 approximately two times per week.

Preparation of RNA: RNA used for C-ORF was prepared either by acid-phenol extraction followed by isopropanol precipitation (35) or by the RNeasy Mini Kit (Qiagen). Precipitated RNA samples for C-ORF were treated with RNase-free DNase and reextracted as for primary RNA. RNA prepared using the RNeasy Mini Kit (Qiagen) was used directly without further treatment. The quality of RNA was determined by examining intact 28S and 18S rRNA bands after resolution in 2% formaldehyde agarose gels (2).

C-ORF method for 5' cDNA end cloning: C-ORF consists of three reaction steps, reverse transcription (RT), second strand synthesis and PCR. RNA samples (2 $\mu$g) are reverse transcribed by SuperScript RT II (RNase H minus MMLV RT, BRL) with minor modifications from the manufacturer's protocol. The modifications include the use of 5 mM DTT instead of 10 mM DTT, 2 pmole gene specific RT primer for oligo dT and inclusion of 5 U RNaseIn. The RT reaction temperature was 45° C. unless specified. First strand cDNA was purified with GlassMax(BRL) after RNase H (2.2 U) plus RNase A (0.5 $\mu$g) digestion for 30 min at 37° C. (50 $\mu$l final). A degenerate stem-and-loop annealing primer (D-SLAP or D-CLAP) was annealed in a 20 $\mu$l mixture of 10 to 16 $\mu$l cleaned first strand cDNA, 2 pmole annealing primer and 2 $\mu$l 10× KlenTaq™ buffer (0.4 M Tricine-KOH, pH 9.2, 0.15 M KOAc, 35 mM Mg $(OAc)_2$ and 37.5 $\mu$g/ml BSA). The annealing mixture was incubated at 95° C. for 1 min and was gradually cooled at 5° C./min to annealing temperature (42° C. unless specified) During the 5 min of incubation at the annealing temperature, the annealing mixture was supplemented with 5 $\mu$l of a polymerase mixture consisting of 0.25 $\mu$l Advantage cDNA polymerase mix™, 0.5 $\mu$l 10 mM dNTPs and 0.5 $\mu$l 10× KlenTaq™ buffer and incubated for 30 min at 68° C. Temperature was controlled using an MJ Minicycler™. Primary PCR was performed in a 25 $\mu$l reaction consisting of 5 $\mu$l of a second strand synthesis reaction mixture, 2.0 $\mu$l 10× KlenTaq™ buffer, 200 $\mu$M dNTPs, 5.0 pmole 3' gene specific primer (GSP), 10 pmole anchor primer and 0.25 $\mu$l Advantage cDNA polymerase mix™. Basic PCR parameter, which varied depending on target size, were as follows: 95° C. for 1 min, 27 cycles of amplification at 95° C. for 30 sec, 58° C. for 1 min and 68° C. for a specified period (1 to 1.5 min per 1 kb target size), and 5 or 10 min further incubation at 68° C. For nested PCR, 0.5 $\mu$l of the primary PCR was used employing essentially the same PCR parameters. Nested PCR reactions (50 $\mu$l) contain 0.5 $\mu$l of primary PCR reaction mixture, 5 $\mu$l 10× KlenTaq™ buffer, 0.2 mM dNTPs, 10 pmole nested GSP, 10 pmole anchor primer and 0.5 $\mu$l Advantage cDNA polymerase mix™. A single primer reaction with GSP only or the anchor primer only is also performed with primary PCR reactions to distinguish C-ORP artifacts. PCR reactions are resolved in 1% agarose gels and bands are purified with a gel purification kit (Qiagen). Purified bands are directly sequenced with anchor primer and GSP.

C-ORF method for 3' cDNA end cloning: Reverse transcription is performed and the product is purified as described in the C-ORF method for 5' end cloning in the previous section except that 10 pmole of the T-SLAP reagent and 5 $\mu$g total RNA are used in place of the GSP. The primary PCR reaction mixture (50 $\mu$l) contains 2 $\mu$l of purified first strand cDNA, 5 $\mu$l 10× KlenTaq™ buffer, 0.2 mM dNTPs, 10 pmole GSP, 10 pmole anchor primer and 0.5 $\mu$l Advantage cDNA polymerase mix™. Nested PCR mixtures consist of the same components except 1 $\mu$l of a 10-fold diluted primary PCR of the first strand cDNA synthesis and substitution of nested GSP for GSP. PCR parameters including temperature and duration are the same as described in the previous section.

Northern and Southern blot hybridizations: RNA samples separated in 2%-formaldehyde agarose gels were transferred to Nylon membranes. Northern blots were hybridized with $^{32}$P-labeled mda-5 3' EST (0.4 kb) or a gel purified C-ORF product (1.8 kb) as previously described (2). A Southern blot was prepared by transferring the PCR samples resolved in a 1% agarose gel to the Nylon membrane after depurination and denaturation. The blot was hybridized with $^{32}$P-labeled nested GSP (MSR4) (Table 1) in 50% formamide hybridization buffer at room temperature.

Results and Discussion

The C-ORF method was designed to obviate the complicated and inefficient steps associated with the conventional RACE procedure, which includes TdT-mediated tailing or single strand oligonucleotide ligation by T4 RNA ligase (16–18, 36). FIG. 1A provides a schematic representation of the C-ORF strategy in which a universal primer site is generated by annealing the D-SLAP reagent to reverse transcribed cDNA during second strand cDNA synthesis. The hairpin (D-SLAP) or clover-leaf (D-CLAP) structure (FIG. 1B) which form bulky loop structures are hypothesized to prevent the degenerate sequences from annealing and extending in the middle of reverse transcribed cDNA because of stearic hindrance. Several restriction sites (Spe I, Xho I, Hinc II) for cloning PCR products into vectos are included in this construct. To ensure formation of the D-SLAP structure prior to association with target cDNA, the length of the stem is made longer than the degenerate sequences (18 vs. 12 nts) and the temperature from denaturation to annealing is gradually decreased (5° C./min) during second strand cDNA synthesis. In order to reduce PCR-related mutation and to enhance long range PCR amplification and specificity, the S advantage cDNA polymerasem mixture (ClonTech, mixture of KlenTaq-1 DNA polymerase, proofreading Deep Vent$_R$™ and TaqStart™ antibody) is used during second strand cDNA synthesis and subsequent PCR amplification (37, 38).

In an attempt to obtain a complete open reading frame for the novel gene mda-5 both library screening, conventional RACE and cap-switching RACE approaches were tried. Even after repeated attempts, these approaches resulted in the cloning of only a 2-kb cDNA library product of mda-5 lacking the complete open reading frame of this gene. In contrast, when the C-ORF cloning approach was used with 2 μg of total RNA from HO-1 cells a complete open reading frame for mda-5. (~3.6 kb) was obtained. Employing an RT temperature of 48° C., an extended mda-S fragment of 1.8 kb was produced by the C-ORF scheme with a single round using the D-SLAP reagent (FIG. 2A).

Figure 2D:
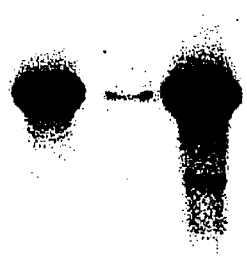
Figure 2E:
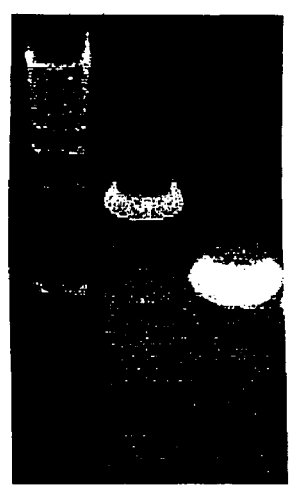

The effect of concentration of the D-SLAP reagent during second strand synthesis and the anchor primer in primary PCR reaction on mda-5 gene amplification using the C-ORF approach were evaluated (FIG. 2B). The specificity of th PCR products produced using the C-ORF approach with the D-SLAP reagent was determined by Southern blot hybridization (FIG. 2C). Specific products of the anticipated size were produced using all of the primer concentrations tested, with the exception of the 40 nM D-SLAP/0.4 μM anchor primer combination. The most effective anchor primer combination in yielding a single specific amplification product employed 80 nM of D-SLAP/0.4 μM anchor primer (FIG. 2B, lane 5). The 1.8 kb mda-5 C-ORF product labeled with $^{32}$P was hybridized to a Northern blot of RNA from HO-1 human melanoma cells treated with recombinant human fibroblast interferon (IFN-β) and detected the same sized band with a similar induction pattern as seen with the previously cloned mda-5 EST (FIG. 1D). Direct sequencing of gel purified products revealed a single ORF contiguous with the previously cloned mda-5 fragment. When compared with the genomic sequence from a mda-5 BAC genomic clone and primer extension results, the cloned mda-5 cDNA identified by C-ORF with the D-SLAP reagent terminated 61 bp downstream from the putative transcription start site (39). RT-PCR with 5' primers designed from the C-ORF derived mda-5 sequence further verified the authenticity of the PCR product as the complete ORF of mda-5 (FIG. 1E).

Figure 3:
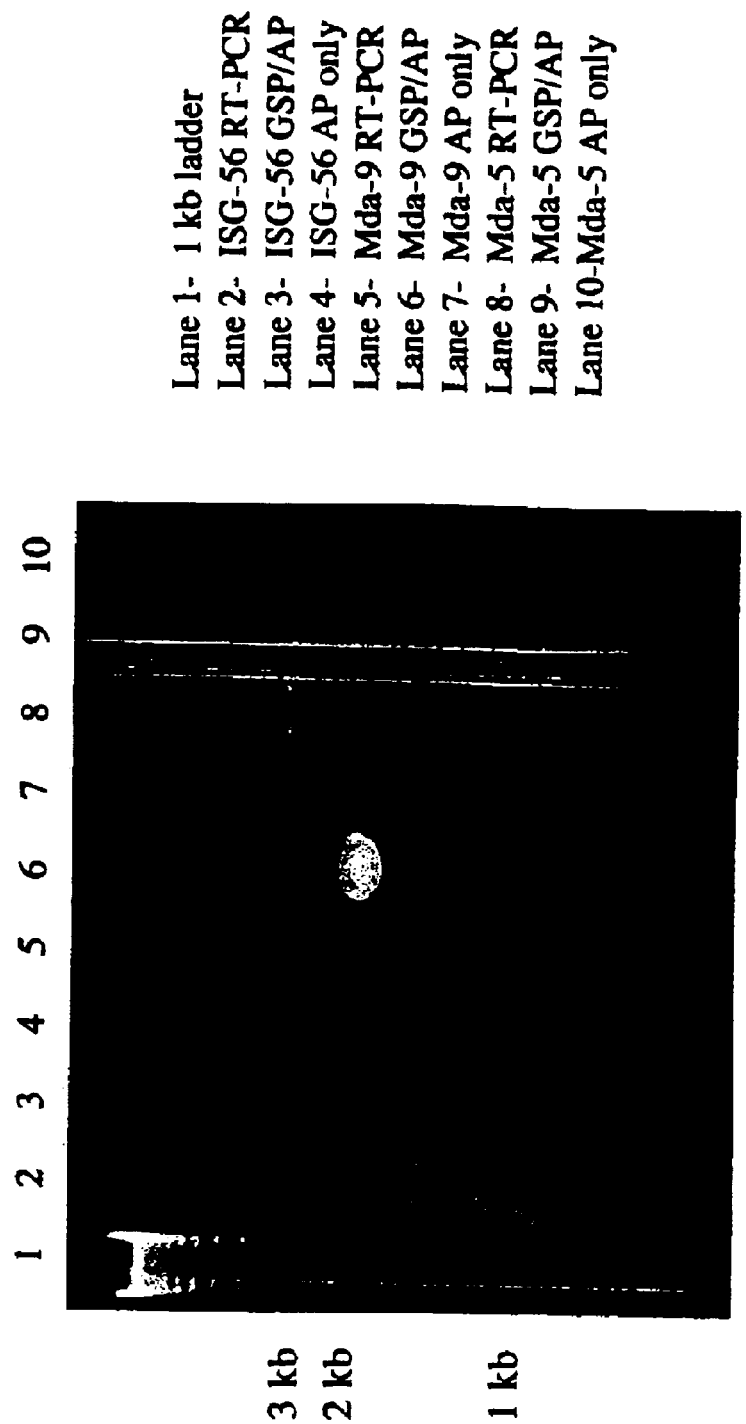
FIG. 3. Applications of the C-ORF protocol for identification of the complete ORF of ISG-56, mda-9 and mda-5. C-ORP products of ISG-56, mda-9 and mda-5 were resolved in 1% agarose gel (lanes 3, 6 and 9). The C-ORF products are shown in comparison with the RT-PCR products of each gene using a common 3' nested primer and a 5' primer from reported gene sequence (lanes 2, 5 and 8). Nested PCR of C-ORF with only an anchor primer (lanes 4, 7 and 10) distinguishes gene specific C-ORP products from RT-PCR artifacts.

To confirm the utility of the C-ORF approach with the D-SLAP reagent for cloning the entire open reading frames from ESTs, studies were performed using three previously cloned genes (ISG-56, 1.5 kb (27); mda-9, 2 kb (28)) and mda-5 (3.6 kb). For comparison, standard RT-PCR was performed with each message with a 5' primer designed from a distal 5' sequence and a 3' primer used in nested PCR reactions with C-ORF. As shown in FIG. 3A, each C-ORF reaction produced a fragment of the predicted size. Although complex banding patterns were seen in the C-ORF reactions versus RT-PCR, distinguishing PCR artifacts was readily accomplished by simultaneously running an anchor-only PCR reaction without the requirement for Southern blot hybridization verification (15). C-ORF-derived PCR products of ISG-56 (1.5 kb) (27) and mda-9 (2 kb) (28) contained the full ORF for these genes, but they lacked 34 nts (ISG-56) and 27 nts (mda-9), respectively, from the complete sequence reported in GenBank. The C-ORF approach with the D-SLAP reagent using mda-5 sequence information generated 2 fragments, a 3 kb product that was identical to that obtained previously and a 1.2 kb fragment representing a prematurely terminated gene product (31). For practical purposes, to obtain the most sequence information and the complete ORF for a given EST, the larger sized fragment would be the optimal fragment to isolate and sequence when performing the C-ORF approach. The appropriate size of the cDNA can also be obtained by Northern blotting analysis using the EST as a probe.

The C-ORF approach with the D-SLAP reagent has been used successfully for obtaining the complete ORF for a number of additional genes. Applications of the C-ORF approach using the D-SLAP reagent with the prostate carcinoma tumor antigen-1 (PCTA-1) gene (29) has resulted in the identification of variants of this gene with sizes of 3.5, 3.2, and 3.0 kb. The C-ORF approach permitted an extension of the 5' UTR sequence reported for PCTA-1 (29) by 400 bp. Additionally, the C-ORF approach with the D-SLAP reagent was used to determine the sequence of a cDNA associated with cellular senescene and terminal cell differentiation, OLD-35 (34). A number of novel ESTs have been identified using an approach called reciprocal subtraction differential RNA display (RSDD) (33). These include novel ESTs that display elevated expression as a function of cancer progression, called progression elevated genes (PEGen), or reduced expression during cancer progression, called progression suppressed genes (PSGen) (33). C-ORF with the D-SLAP reagent has been used to generate a complete open reading frame for PEGen 28 (1.6 kb), PEGen 42 (1.8 kb) and PSGen 12 (1.2 kb).

Although the reaction temperature of RT profoundly affects the efficiency of C-ORF for genes like mda-5, a high RT temperature is not mandatory for other C-ORF applications (RT can be performed at 42 to 45° C). RT temperature-dependence may be a consequence of extensive secondary structure at the 5' UTR of specific cDNAs (6). An initial application of the C-ORF approach for cloning OLD-35 produced a shorter than anticipated product where a strong hairpin structure is predicted (34). However, an additional round of C-ORF produced a full ORF of OLD-35. Numerous attempts to clone OLD-35 by conventional RACE only yielded a few hundred-bp PCR product and further extension using different primer sets was not possible. In general, increasing RT temperature should prove helpful in assuring first strand cDNA synthesis to the end of the transcript by overcoming secondary structure of the RNA (21). By using RNase H-minus MMLV-RT (Superscript II), reverse transcription can be efficiently performed up to 48° C. and even higher temperatures (55 to 65° C.) can be achieved using commerically available thermostable RT (14,21).

Second strand cDNA synthesis appears to depend on the D-SLAP concentration with lower concentrations of the D-SLAP reagent being less effective in promoting second strand cDNA synthesis (FIG. 2B lane 2 and 3). Additional experiments suggest that the concentration of the D-SLAP reagent should be higher than 20 nM. Combinations of different anchor-gene specific primer (GSP) concentration ratios in the primary PCR were also tested for ISG-56. Combinations of 0.2 or 0.4 μM anchor plus 0.2 μM GSP produced an appropriate sized PCR product. However, the yield of PCR product was generally higher when using concentrations of 0.4 μM anchor and 0.2 μM GSP. Since 0.4 pmole of the D-SLAP reagent (⅕ of the second strand cDNA synthesis reaction) is carried over to the primary PCR reaction and it contains anchor primer binding sites, it may be necessary to use additional anchor primers to obtain appropriate PCR amplification. Thus, it is possible that the inefficient second strand cDNA synthesis at low D-SLAP and high anchor primer concentrations can result in a high yield of non-specific PCR products in mda-5 (FIG. 1B, lane 3).

Parameters for D-SLAP reagent annealing during second strand cDNA synthesis, including annealing temperature, temperature ramping and single tube second strand cDNA synthesis followed by PCR, were further investigated with mda-9 (28) and ISG-56 (27). It was found that annealing temperatures up to 50° C. were as effective as 42° C., and in certain cases superior to the lower temperature. Moreover, as observed with ISG-56 (27), an annealing temperature higher than 46° C. yielded a less complex pattern of C-ORF products. The annealing temperature used for C-ORF is considerably higher than the calculated $T_M$ (44.5° C.) for the D-SLAP priming site sequence of ISG-56 (27). It appears that raising the annealing temperature prevents priming of D-SLAP reagents to relatively weak internal sites. A similar temperature dependence was also observed in single tube second strand cDNA synthesis and PCR, but the overall production of the appropriate PCR product in the single tube reaction was significantly lower than that of the standard C-ORF protocol. This probably results because the D-SLAP reagent containing the anchor primer site may interfere with subsequent PCR processivity. Rapid ramping to 85° C. followed by a gradual decrease to the annealing temperature (42° C., 5° C./min) or the addition of pre-annealed D-SLAP reagent did not significantly enhance PCR yield as compared with the standard C-ORF protocol.

The results described above clearly demonstrate the efficiency of C-ORF with the D-SLAP reagent in cloning the open reading frame of a cDNA using EST information. However, although C-ORF effectively extends cDNAs to include the complete ORF, it did not extend the product to the end of the transcript. Provided that the stem and loop structure of the D-SLAP reagent prevents degenerate sequences from binding to internal sites as predicted, it is possible that the RT did not extend to the 5' end of the transcript. Alternatively, the D-SLAP reagent may bind to internal sites during second strand cDNA synthesis resulting in the generation of a shorter product. The 5' end of sequences of ten C-ORF products where the degenerate region of D-SLAP reagent primed are summarized in Table 2. Considering that the G/C content of the 12 bp 5' sequences are 71% on average or 100% for mda-5 (31) and mda-9 (28), respectively, it appears that the annealing of the D-SLAP reagent is not completely sequence-independent but rather prefers G/C rich regions. In fact, C-ORF PCR yields are higher for mda-9 (28) than for ISG-56 (27), although the RT-PCR yields of the two products are similar. Furthermore, while ISG-56 (27) C-ORF largely depends on which second strand cDNA synthesis procedure is used, mda-9 (28) is easily amplified by most of the protocols tested.

Current data suggests that the target sequence used in C-ORF is important, but it is not the most critical determinant for annealing of the D-SLAP reagent to target sequences. Sequence analysis of 12 bp stretches in mda-9 reveals one G/C site of 12/12, one G/C site of 11/12, one G/C site of 10/12 and three G/C sites of 9/12 (28). The C-ORF product of mda-9 begins at the highest G/C content site that is located 27 bp downstream of the reported cDNA end of this cDNA. Although the D-SLAP reagent annealed to the highest G/C rich site in mda-9, based on the sequence analysis of annealing sites (Table 2) this primer could also have annealed to other sites with>75% G/C content in mda-9. In contrast, the D-SLAP reagent annealed to ISG-56 at the 58.3% G/C content site, whereas ISG-56 has two 12 bp stretches of 10/12 G/C and 6 sites of 9/12 G/C, respectively (27). If the G/C sequence content were the primary determinant of D-SLAP annealing and assuming a preference bias of PCR for shorter fragments, C-ORF applied to ISG-56 would be predicted to generate a mixture of products including the annealing site containing the 58.3% G/C content. The D-SLAP reagent could potentially anneal to all of the G/C rich fit sites, but the C-ORF product of ISG-56 that was amplified by PCR derived from a site of lower G/C content (58.3%) than the average G/C content of D-SLAP annealing sites (71%).

The propensity of C-ORF to generate near-end products may result either from preferential second strand cDNA synthesis when the D-SLAP reagent is annealed at the 3' end of the first strand cDNA or from an unanticipated PCR bias for the annealed D-SLAP reagent. In either case, the stem-and-loop structure of D-SLAP certainly plays a significant role in the preferential production of near-end fragments when using the C-ORF method. This bias may result by structurally preventing efficient second strand cDNA synthesis from deep internal sites within the cDNA. By providing a rigid stem-and-loop structure at the annealing temperature, it is possible that the longer stretch of DNA in the displaced strand that results from D-SLAP annealing has a greater chance to interfere with second strand cDNA synthesis. This may occur either by forming a complex secondary structure or by an undefined interaction of the displaced DNA strand with the D-SLAP reagent.

Figure 4A:
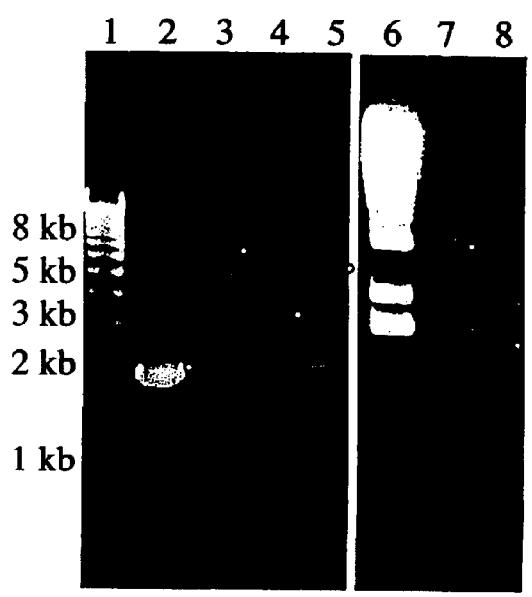
FIGS. 4A–4B. C-ORF protocol with the D-CLAP1 and D-CLAP2 reagents for 5' cDNA end cloning.

It is assumed that the stem-and-loop structure of D-SLAP facilitates second strand cDNA synthesis from the end or near the end of the cDNA. In this context, degenerate clover-leaf annealing primers (D-CLAP), containing three stem-and-loop structures, might even be more effective than the D-SLAP reagent in inhibiting second strand cDNA synthesis from internal priming sites, thereby alleviating the G/C sequence-dependence of D-SLAP. It is also established that RT has TdT-like activity and can add multiple Cs at the 3' end of the first strand cDNA from capped RNA (10,11). Based on these considerations, we designed two D-CLAP reagent, D-CLAP1 and D-CLAP2. While the D-CLAP1 reagent contains an annealing site with the sequence GGGN10, the D-CLAP2 reagent contains 13 random oligonucleotides. C-ORF with the D-CLAP1 and D-CLAP2 reagents was performed with ISG-56 (27), mda-9 (28), mda-5, PCTA-1 from either poly A site (3.5 and 5 kb, respectively (29, 39) and fibronectin (8 kb) (30). A single round of the C-ORF approach performed with the D-CLAP1 reagent generated bands of the expected size, not only for shorter transcripts (ISG-56 and mda-9) but also for larger transcripts (PCTA-1/pA and fibronectin) (FIG. 4A), although this approach did increase band complexity. The annealing site sequence of ISG-56 is further upstream of the C-ORF product performed using the D-SLAP reagent, but it is still shorter than the reported gene sequence by 11 nts (27). In contrast, the C-ORF derived fragment of PCTA-1 obtained using the D-CLAP1 reagent is shorter than that obtained using the D-SLAP reagent, but it is longer than the reported sequence (29, 39). Although C-ORF with the D-CLAP1 reagent successfully supports cDNA cloning up to 8-kb transcript size (close to the limit of PCR), as expected it appears not to anneal to the CCC-tail generated by RT-TdT like activity (10, 11).

Figure 4B:
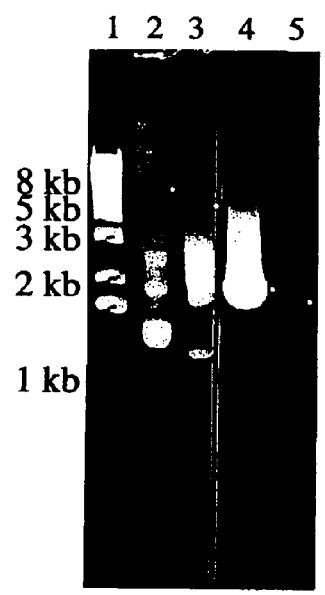

The full protein coding region of ISG-56 (27), mda-9 (28), mda-5 (31), PCTA-1 (3.5 kb and 5 kb) (29, 39) and fibronectin (30) could also be amplified using the C-ORF approach with the D-CLAP2 reagent (random 13 bp annealing site, FIG. 4B). Compared with the C-ORF approach using the D-CLAP1 reagent, the D-CLAP2 reagent clearly reduced band complexity, although in general it generated shorter sized fragments (43 bp short in PCTA-1). With increasing target size, the complexity of the PCR generated products increased when performing C-ORF with either the D-CLAP1 or D-CLAP2 reagent. The increased band complexity obtained when using C-ORF with long cDNA targets may occur because the RT pre-termination (6) and internal priming sites overcome the stearic interference of the stem-and-loop structure of the D-CLAP reagents. C-ORF with the D-CLAP1 reagent seems to be more dependent on target sequence than C-ORF with the D-CLAP2 reagent since the GGG sequence stretch upstream of the random sequence in the D-CLAP1 reagent can more strongly direct primer annealing and subsequent extension than the D-CLAP2 reagent. Attempts to directly sequence the D-CLAP1 reagent C-ORF product with the anchor primer were unsuccessful, probably because of the hairpin structure in the anchor primer and the heterogeneous annealing of the GGG stretch, e.g., GGG can anneal in either direction to CCCC or CCCC. Provided that C-ORF with the D-CLAP2 reagent can yield the full protein coding region as exemplified in a number of applications, C-ORF using the D-CLAP2 reagent would be preferable to performing C-ORF with the D-CLAP1 reagent.

Figure 5:
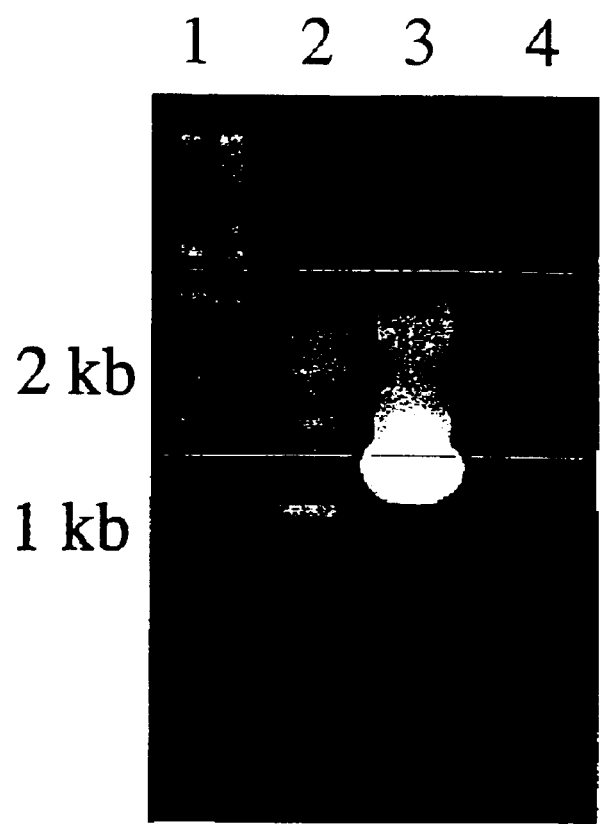
FIG. 5. C-ORF with the T-SLAP reagent for 3' cDNA end cloning. Products of 3' C-ORF of PCTA-1 using the T-SLAP reagent were resolved in a 1% agarose gel. Nested PCR products produced with the anchor primer only (lane 2), both anchor primer and GSP (lane 3) and GSP only (lane 4). DNA sizing ladder (lane 1).

The utility of the D-SLAP reagent and C-ORF in cloning the 3' end of a cDNA was investigated to determine if this method could be used to obtain a complete 3' UTR of the PCTA-1 cDNA (29). An oligo-dT stem and loop annealing primer (T-SLAP) was made by replacing oligo-dT for the random sequence of the D-SLAP reagent and was included in an RT reaction during the C-ORF procedure. PCR amplification (primary and nested) resulted in a specific 1.2-kb fragment, which was confirmed by genomic sequence and RT-PCR as PCTA-1 (FIG. 5). The same protocol was also applied to 31 end cloning of OLD-35 (34), PEGen 28 and PEGen 50 (33) resulting in a 0.5 to 1 kb PCR amplification product corresponding to the 3' region of these cDNAs. These results indicate that primers based on a stem-and-loop structure can be efficiently used for both 51 and 3' end cloning of cDNAs.

Although the C-ORP method employs a common strategy involving a single side specific PCR reaction that is also used in the conventional RACE approach (14), C-ORF is unique in the generation of a universal anchor primer site and in the second strand cDNA synthesis step. Instead of homopolymer-tailing by TdT (15, 16) or single strand oligonucleotide ligation by T4 RNA ligase to the first strand cDNA (17,18), C-ORF involves the annealing of the D-SLAP or D-CLAP reagent to the first strand cDNA. By annealing degenerate primers, the C-ORF method eliminates an inherent problem of the conventional RACE approach caused by the inefficiency and sequence-dependence of the TdT and T4 RNA ligase reactions and the purification procedures required after the reaction (13, 23). Furthermore, since Taq polymerase is used during second strand cDNA synthesis and in the subsequent PCR reaction, no additional enzymes are required for the reaction. The complicated ramping to annealing temperature should not pose a problem, since most commercial thermocyclers have a program for gradual temperature declination. Compared with the conventional RACE approach, the C-ORF protocol represents a significant improvement resulting in less band complexity and a dramatic increase in the size of the cloned PCR generated product (13, 16–18, 20.) Although the anchor primer can on occasion generate PCR artifacts, it is easy to identify these spurious products by running anchor primer samples side by side with anchor primer plus GSP samples. This eliminates the need for Southern blot hybridization to confirm the gene specific authenticity of the PCR amplified product (15). A prominent feature of C-ORF that distinguishes it from the conventional and modified RACE approaches is that C-ORF yielded full protein coding regions in a single application in 9 out of 10 test cases. Targets as small as 0.3 kb and as large as 8 kb could be amplified by the C-ORF protocol in a single reaction. These results confirm that the C-ORF approach will have wide applcability for identifying the complete protein coding regions of most ESTs and in many cases this will be acheived by a single application of the C-ORF methodology.

Applications of the C-ORF approach for cloning the complete open reading frame of diverse genes demonstrates that this approach is an efficient and simple way of cloning both 3' and 5' ends of cDNAs from EST sequences. With a small amount of starting material (⅕ to ⅓ of an RT reaction with 2 μg of total RNA), C-ORF efficiently amplifies the complete protein coding region of diverse genes in most cases without the need for repetitive applications. Although in its present form C-ORF does not appear applicable for identifying the transcription start site, C-ORF is a cost-, time- and laborsaving method over currently used methods such as library screening and RACE for quickly obtaining biologically meaningful sequence data produced by C-ORF permits a determination of the uniqueness of the reported ESTs and provides sufficient information to procure corresponding clones from various providers to rapidly determine the full-length sequence of the gene. The quickness, ease of performance and efficiency of the C-ORF approach enables one to pursue multiple cDNA cloning projects simultaneously, which is necessary to expedite ongoing genome projects.

Additionally, since D-SLAP or D-CLAP primers anneal to random sequence and provide primer sites, the primers can also be used for genomic cloning or cloning cDNA of a family of genes in case that partial sequence of the target fragment is known. Furthermore, the structural motif of D-SLAP or D-CLAP potentially inhibits transcription and/or translation if specific sequence in substitution of random sequence for a target molecule is designed to anneal to the molecule in reverse orientation. In case, D-SLAP or D-CLAP primer can be used for blocking function of specific gene and can be an alternative way of gene therapy. Also, if the bulky structure of D-SLAP or D-CLAP is antigenic enough to raise antibody, specific sequence in substitution of random sequence can be useful for sequence-specific capture of nucleic acids.

In conclusion, C-ORF with its simplicity, versatility and long-range capability can significantly contribute to genome discovery efforts by overcoming the rate limiting full length cDNA cloning step required for defining and functionally evaluating the numerous ESTs and incomplete cDNAs that continue to be identified.

TABLE 1

Sequence of gene specific primers used in the C-ORF cloning technology.

| Primer | Gene   | Sequence                                                      |
|--------|--------|---------------------------------------------------------------|
| AP-1   | D-SLAP | 5'-TTCTGGTCGACTAGTGTTTAAACTCGAGAC-3' (SEQ ID NO:1)             |
| AP-2   | D-SLAP | 5'-CACGATCAGTCGACGAAGTCGACACTCGAG-3' (SEQ ID NO:2)             |
| M5R1   | mda-5  | 5'-TTTTTTTTTTTTCAGAGTAAAACAATC-3' (SEQ ID NO.3)                |
| M5R2   | mda-5  | 5'-TGTGCACCATCATTGTTCCCCAAGCC-3' (SEQ ID NO:4)                 |

TABLE 1-continued

Sequence of gene specific primers used in the C-ORF cloning technology.

| Primer | Gene | Sequence |
|---|---|---|
| M5R3 | mda-5 | 5'-AATCTGACATTGGACTCATTTGAC-3' (SEQ ID NO:5) |
| M5R4 | mda-5 | 5'-GTTTGAATCCTTGTCATTATTTCTAG-3' (SEQ ID NO:6) |
| M5S1 | mda-5 | 5'-GCCTGAGAGCCCTGTGGACAACCTCG-3' (SEQ ID NO:7) |
| 56R1 | ISG-56 | 5'-GTGGCTGATATCTGGGTGCCTAAGG-3' (SEQ ID NO:8) |
| 56R2 | ISG-56 | 5'-CCTAAGGACCTTGTCTCACAGAGTTC-3' (SEQ ID NO:9) |
| 56S1 | ISG-56 | 5'-CCAGATCTCAGAGGAGCCTGGCTAAGC-3' (SEQ ID NO:10) |
| M9R1 | mda-9 | 5'-AATCAGGATAAAGTGTCAACTATC-3' (SEQ ID NO:11) |
| M9R2 | mda-9 | 5'-ATCCCAAAGTAGCTAGGTTACATAATC-3' (SEQ ID NO:12) |
| M9S1 | mda-9 | 5'-CCTCAGAAGTCCGTGCCAGTGACCGG-3' (SEQ ID NO:13) |
| FnR1 | fibronectin | 5'-TTTTTTTTTTTTGTGGAATGTAAATC-3' (SEQ ID NO:14) |
| FnR2 | fibronectin | 5'-AGATGGATCTTGGCAGAGAGACATGC-3' (SEQ ID NO:15) |
| PCTAR1 | PCTA-1 | 5'-GAAGAAGTAGAACATCAGTGCC-3' (SEQ ID NO:16) |
| PCTAR2 | PCTA-1 | 5'-TCTTCTGTACAGCAGTATCTTACAT-3' (SEQ ID NO:17) |
| PCTAR3 | PCTA-1 | 5'-TTTTTTTTTTTTTTTTGTTTGCATGCGG-3' (SEQ ID NO:18) |
| PCTAR4 | PCTA-1 | 5'-TTACAAACAGCTCCCAAATGGTGAAACT-3' (SEQ ID NO:19) |

TABLE 2

Sequence of the 5' end of the C-ORF products.

| Name | 5' sequence | | G/C score | % G/C |
|---|---|---|---|---|
| mda-20 | 5'-GCGCGCCGGCCT-3' | (SEQ ID NO:20) | 11/12 | 91.7 |
| ISG-56 | 5'-TGCAGAACGGCT-3' | (SEQ ID NO:21) | 7/12 | 58.3 |
| mda-9 | 5'-GGCGGCGGCGGC-3' | (SEQ ID NO:22) | 12/12 | 100.0 |
| PCTA-1A | 5'-TGGAGGCCTGGA-3' | (SEQ ID NO:23) | 8/12 | 66.7 |
| PCTA-1B | 5'-GCCAGTGCCTCA-3' | (SEQ ID NO:24) | 8/12 | 66.7 |
| PCTA-1C | 5'-CGATGTGGCCTT-3' | (SEQ ID NO:25) | 7/12 | 58.3 |
| OLD-35 | 5'-CGGAGGACCAAT-3' | (SEQ ID NO:26) | 7/12 | 58.3 |
| PSGen 12 | 5'-GCGGTGGTGACG-3' | (SEQ ID NO:27) | 9/12 | 75.0 |
| PSGen 28 | 5'-GTGTGGTGTGTC-3' | (SEQ ID NO:28) | 7/12 | 58.3 |
| PSGen 42 | 5'-GGCGTTGCGACG-3' | (SEQ ID NO:29) | 9/12 | 75.0 |
| G/C/ score | 8994867986 74 | | 85/120 | 70.8 |

REFERENCES

17. Adams, M. D., Kerlavage, A. R., Fleischmann, R. D., Fulder, R. A., Bult, C. J., Lee, N. H., Kirkness, E. F., Weinstock, K. G., Gocayne, J. D., White, O., et al. Initial assessment of human gene diversity and expression patterns based upon 83 million nucleotides of cDNA sequence, Nature. 377 (Suppl.): 3–174, 1995.
18. Sambrook, J., Fritsch, E., and Maniatis, T. Molecular Cloning, 2nd edition. New York, N.Y.: Cold Spring Harbor Laboratory Press, 1989.
19. Frohman, M. On beyond RACE, PCR Methods Application. 4: S40-S58, 1994.
20. Duyk, G. M., Kim, S. W., Myers, R. M., and Cox, D. R. Exon trapping: a genetic screen to identify candidate transcribed sequences in cloned mammalian genomic DNA, Proc Natl Acad Sci USA. 87: 8995–8999, 1990.
21. Auch, D. And Reth, M. Exon trap cloning: using PCR to rapidly detect and clone exons from genomic DNA fragments, Nucleic Acids Res. 18: 6743–6744, 1990.
22. Kotewicz, M. L., Sampson, C. M., D'Alessio, J. M., and Gerard, G. F. Isolation of cloned Moloney murine leukemia virus reverse transcriptase lacking ribonuclease H activity, Nucleic Acids Res. 16: 265–277, 1988.
23. D'Alessio, J. M. and Gerard, G. F. Second-strand cDNA synthesis with E. coli DNA polymerase I and RNase H: the fate of information at the mRNA 5' terminus and the effect of E. coli DNA ligase, Nucleic Acids Res. 16: 1999–2014, 1988.
24. Carninci, P., Kvam, C., Kitamura, A., Ohsumi, T., Okazaki, Y., Itoh, M., Kamiya, M., Shibata, K., Sasaki, N., Izawa, M., Muramatsu, M., Hayashizaki, Y., and Schneider, C. High-efficiency full-length cDNA cloning by biotinylated CAP trapper, Genomics. 37: 327–336, 1996.
25. Kato, S., Sekine, S., Oh, S. W., Kim, N. S., Umezawa, Y., Abe, N., Yokoyama-Kobayashi, M., and Aoki, T. Construction of a human full-length cDNA bank, Gene. 150: 243–250, 1994.
26. Hirzmann, J., Luo, D., Hahnen, J., and Hobom, G. Determination of messenger RNA 5'-ends by reverse transcription of the cap structure, Nucleic Acids Res. 21: 3597–3598, 1993.

27. Bahring, S., Sandig, V., Lieber, A., and Strauss, M. Mapping of transcriptional start and capping points by a modified 5' RACE technique, Biotechniques. 16: 807–808, 1994.
28. CapFinder PCR cDNA Synthesis Kit, CLONTECHniques. 11: 2–4, 1996.
29. Hooft van Huijsduijnen, R. PCR-assisted cDNA cloning: a guided tour of the minefield, Riotechniques. 24: 390–392, 1998.
30. Schaefer, B. C. Revolutions in rapid amplification of cDNA ends: new strategies for polymerase chain reaction cloning of full-length cDNA ends, Anal Biochem. 227: 255–273, 1995.
31. Frohman, M. A., Dush, M. K., and Martin, G. R. Rapid production of full length cDNAs from rare transcripts: amplifications using a single gene-specific oligonucleotide primer, Proc Natl Acad Sci USA. 85: 8998–9002, 1988.
32. Loh, E. Y., Elliot, J. F., Cwirla, S., Lanier, L. L., and Davis, M. M. Polymerase chain reaction with single-sided specificity: analysis of T cell receptor delta chain, Science. 243: 217–220, 1989.
33. Troutt, A. B., McHeyzer-Williams, M. G., Pulendran, B., and Nossal, G. J. Ligation-anchored PCR: a simple amplification technique with single-sided specificity, Proc Natl Acad Sci USA. 89: 9823–9825, 1992.
34. Edwards, J. B., Delort, J., and Mallet, J. Oligodeoxyribonucleotide ligation to single-standed cDNAs: a new tool for cloning 5' ends of mRNA and for constructing cDNA libraries by in vitro amplification, Nucleic Acids Res. 19: 5227–5232, 1991.
35. Liu, X. And Corovsky, M. A. Mapping the 5' and 3' ends of Tetrahymena thermophila mRNAs using RNA ligase mediated amplification of cDNA ends (RLM-RACE), Nucleic Acids Res. 21: 4954–4960, 1993.
36. Frohman, M. RACE: Rapid Amplification of cDNA Ends. In: M. Innis, D. Gelfand, J. Sninsky, and T. White (eds.), PCR Protocols, pp. 28–38. San Diego, Calif.: Academic Press, 1990.
37. Carninci, P., Nishiyama, Y., Westover, A., Itoh, M., Nagaoka, S., Sasaki, N., Okazaki, Y., Muramatsu, M., and Hayashizaki, Y. Thermostabilization and thermoactivation of thermolabile enzymes by trehalose and its application for the synthesis of full length cDNA, Proc Natl Acad Sci USA. 95: 520–524, 1998.
38. Rychlik, W. In: B. White (ed.) Methods in Molecular Biology, Vol. 15, pp. 31–40. Totowa, N.J.: Humana Press, 1993.
39. Chenchik, A., Diachenko, L., Moqadam, F., Tarabykin, V., Lukyanov, S., and Siebert, P. D. Full-length cDNA cloning and determination of mRNA 5' and 3' ends by amplification of adaptor-ligated cDNA, Biotechniques. 21: 526–534, 1996.
40. Maunders, M. DNA and RNA ligases. In: M. Burrell (ed.) Methods of Molecular Biology. Enzymes of Molecular Biology, Vol. 16, pp. 213–230. Totowa, N.J.: Humana Press, 1993.
41. Maruyama, K. And Sugano, S. Oligo-capping: a simple method to replace the cap structure of eukaryotic mRNAs with oligoribonucleotides, Gene. 138: 171–174, 1994.
42. Fromont-Racine, m., Bertrand, E., Pictet, R., and Grange, T. A highly sensitive method for mapping the 5' termini of mRNAs, Nucleic Acids Res. 21: 1683–1684, 1993.
43. Wathelet, M., Moutschen, S., Defilippi, P., Cravador, A., Collet, M., Huez, G., and Content, J. Molecular cloning, full-length sequence and preliminary characterization of a 56-kDa protein induced by human interferons, Eur J Biochem. 155: 11–17, 1986.
44. Lin, J. J., Jiang, H., and Fisher, P. B. Melanoma differentiation associated gene-9, mda-9, is a human gamma interferon responsive gene, Gene. 207: 105–110, 1998.
45. Su, Z.-z., Lin, J., Shen, R., Fisher, P. E., Goldstein, N. I., and Fisher, P. B. Surface-epitope masking and expression cloning identifies the human prostate carcinoma tumor antigen gene PCTA-1 a member of the galectin gene family, Proc Natl Acad Sci USA. 93: 7252–7257, 1996.
46. Kornblihtt, A. R., Umezawa, K., Vibe-Pedersen, K., and Baralle, F. E. Primary structure of human fibronectin: differential splicing may generate at least 10 polypeptides from a single gene, EMBO J. 4: 1755–1759, 1985.
47. Kang, D.-c. and Fisher, P. B. Unpublished results, 1999.
48. Jiang, H. and Fisher, P. B. Use a Sensitive and Efficient Subtraction Hybridization Protocol for the Identification of Genes Differentially Regulated during the Induction of Differentiation in Human Melanoma Cells., Molecular Cellular Differentiation, 1: 285–299, 1993.
49. Kang, D.-c., LaFrance, R., Su, Z.-z, and Fisher, P. B. Reciprocal subtraction differential RNA display: an efficient and rapid procedure for isolating differentially expressed gene sequences, Proc Natl Acad Sci USA. 95: 13788–13793, 1998.
50. Leszczyniecka, M. and Fisher, P. B. Unpublished results, 1999.
51. Chomczynski, P. And Sacchi, N. Single-step method of RNA isolation by acid guanidinum thiocyanate-phenol-chloroform extraction, Anal Biochem. 162: 156–159, 1987.
52. Prohman, M. A. Rapid amplification of complementary DNA ends for generation of full-length complementary DNAs: thermal RACE, Methods Enzymol. 218: 340–356, 1993.
53. Chencik, A., Diachenko, L., Chang, C., and Kuchibhatla, S. Great lengths cDNA synthesis kit for high yields of full-length cDNA, CLONTECHniques. 9: 9–12, 1994.
54. Kellogg, D. E., Rybalkin, I., Chen, S., Mukhamedova, N., Vlasik, T., Siebert, P. D., and Chenchik, A. TaqStart Antibody: "hot start" PCR facilitated by a neutralizing monoclonal antibody directed against Taq DNA polymerase, Biotechniques. 16: 1134–1137, 1994.
55. Gopalkrishnan, R. V. and Fisher, P. B. Unpublished results, 1999.

What is claimed is:

1. A method for isolating a double-stranded cDNA having a nucleotide sequence of a complete open reading frame which comprises:
   A) admixing
      (i) an isolated single-stranded cDNA,
      (ii) a first primer capable of forming a stem-loop structure, comprising
         (a) at the 3' end of the primer, a first, random, sequence, linked to
         (b) a second sequence, linked to
         (c) a third sequence which forms a loop structure, linked to
         (d) a fourth sequence, at the 5' end of the first primer, which is complementary to the second sequence,
         under hybridization conditions sufficient for annealing the first sequence of the first primer to the sequence at the 3' end of the single-stranded cDNA, and
      (iii) a polymerase;
   B) incubating the mixture from step (A) under suitable conditions for DNA synthesis; and
   C) performing a polymerase chain reaction by admixing
      (i) an aliquot of the mixture from (B),
      (ii) a second primer which specifically binds to the single-stranded cDNA generated by step (B),
      (iii) a third primer which comprises
         (a) a sequence identical to the third sequence of the first primer, linked to
         (b) a sequence identical to a portion of the second sequence of the first primer, and
      (iv) a polymerase
      under conditions suitable for a polymerase chain reaction so as to produce a double-stranded cDNA reaction product, thereby isolating the cDNA having the sequence of the complete open reading frame.

2. The method of claim 1, wherein the single-stranded cDNA is a 5' portion of a cDNA reverse transcribed from an mRNA.

3. The method of claim 1, wherein the first primer has the sequence 3'-NNNNNNNNNNNNCAGAGCTCAAATTTG-TGATCAGCTGGTCTTTCACAAATTTGAGCTCTG-5' (D-SLAP; SEQ ID NO:30).

4. The method of claim 1, wherein the first primer has the sequence 3'-NNNNNNNNNGGGAGAGCTCACAGCT-GAAGCAGCTGACTAGCACCTAGTGTAGAATACAT-CTTGAGCTAT-5' (D-CLAP1; SEQ ID NO:31).

5. The method of claim 1, wherein the first primer has the sequence 3'-NNNNNNNNNNNNNAGAGCTCACAGCT-GAAGCAGCTGACTAGCACCTAGTGTAGAATACATC-TTGAGCTAT-5' (D-CLAP2; SEQ ID NO:32).

6. The method of claim 1, wherein the first primer comprises an inosine nucleotide.

7. The method of claim 1, wherein the loop structure is a hairpin-like loop structure, or a cloverleaf loop structure comprising more than one hairpin-like loop structure.

8. A method for isolating a double-stranded cDNA having a nucleotide sequence of a complete open reading frame which comprises:
   A) admixing
      (i) a biological sample containing mRNA comprising a polyA sequence,
      (ii) a first primer which forms a stem-loop structure, comprising:
         (a) a poly-T sequence at the 3' end of the primer linked to
         (b) a first, random, sequence, linked to
         (c) a second sequence which forms a loop structure, linked to
         (c) a third sequence at the 5' end of the primer which is complementary to the first sequence, and
      (iii) a reverse transcriptase, under hybridization conditions sufficient for annealing the primer to the mRNA poly-A sequence;
   B) incubating the mixture from step (A) under suitable conditions for reverse transcription;
   C) performing a polymerase chain reaction with an aliquot of the mixture from step (B) using a second, gene-specific, primer which is pre-defined and a third primer, which has a sequence identical to at least a portion of the first primer sequence, thereby isolating the cDNA having the sequence of the complete open reading frame.

9. The method of claim 8, wherein the primer has the sequence 3'-TTTTTTTTTTTTCAGAGCTCAAATTGTG-ATCAGCTGGTCTTFCACAAATTTGAGCTCTG-5' (T-SLAP; SEQ ID NO:33).

* * * * *

SEQUENCE LISTING

<160> NUMBER OF SEQ ID NOS: 33

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide primer AP-1

-continued

```
<400> SEQUENCE: 1
ttctggtcga ctagtgttta aactcgagac                                    30

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide primer AP-2

<400> SEQUENCE: 2
cacgatcagt cgacgaagtc gacactcgag                                    30

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer M5R1

<400> SEQUENCE: 3
tttttttttt ttcagagtaa aacaatc                                       27

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide primer M5R2

<400> SEQUENCE: 4
tgtgcaccat cattgttccc caagcc                                        26

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer M5R3

<400> SEQUENCE: 5
aatctgacat tggactcatt tgac                                          24

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primer M5R4

<400> SEQUENCE: 6
gtttgaatcc ttgtcattat ttctag                                        26

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer M5S1

<400> SEQUENCE: 7
gcctgagagc cctgtggaca acctcg                                        26
```

```
<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer 56R1

<400> SEQUENCE: 8
gtggctgata tctgggtgcc taagg                                   25

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide primer 56R2

<400> SEQUENCE: 9
cctaaggacc ttgtctcaca gagttc                                  26

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer 56S1

<400> SEQUENCE: 10
ccagatctca gaggagcctg gctaagc                                 27

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer M9R1

<400> SEQUENCE: 11
aatcaggata aagtgtcaac tatc                                    24

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer M9R2

<400> SEQUENCE: 12
atcccaaagt agctaggtta cataatc                                 27

<210> SEQ ID NO 13
<211> LENGTH: 26
<212> TYPE: DNA
<213> ORGANISM: Artificial Sequence
<220> FEATURE:
<223> OTHER INFORMATION: Oligonucleotide primer M9S1

<400> SEQUENCE: 13
cctcagaagt ccgtgccagt gaccgg                                  26

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide primer FnR1
```

-continued

```
<400> SEQUENCE: 14
tttttttttt ttgtggaatg taaatc                                          26

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide primer FnR2

<400> SEQUENCE: 15
agatggatct tggcagagag acatgc                                          26

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer PCTAR1

<400> SEQUENCE: 16
gaagaagtag aacatcagtg cc                                              22

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer PCTAR2

<400> SEQUENCE: 17
tcttctgtac agcagtatct tacat                                           25

<210> SEQ ID NO 18
<211> LENGTH: 29
<212> TYPE: DNA
<213> ORGANISM: Artificial Sequence
<220> FEATURE:
<223> OTHER INFORMATION: Oligonucleotide primer PCTAR3

<400> SEQUENCE: 18
tttttttttt tttttttgtt tgcatgcgg                                       29

<210> SEQ ID NO 19
<211> LENGTH: 28
<212> TYPE: DNA
<213> ORGANISM: Artificial Sequence
<220> FEATURE:
<223> OTHER INFORMATION: Oligonucleotide primer PCTAR4

<400> SEQUENCE: 19
ttacaaacag ctcccaaatg gtgaaact                                        28

<210> SEQ ID NO 20
<211> LENGTH: 12
<212> TYPE: DNA
<213> ORGANISM: Artificial Sequence
<220> FEATURE:
<223> OTHER INFORMATION: Sequence of the 5' end of the C-ORF product of
      mda-5

<400> SEQUENCE: 20
gcgcgccggc ct                                                         12
```

```
<210> SEQ ID NO 21
<211> LENGTH: 12
<212> TYPE: DNA
<213> ORGANISM: Artificial Sequence
<220> FEATURE:
<223> OTHER INFORMATION: Sequence of the 5' end of the C-ORF product of
      ISG-56

<400> SEQUENCE: 21
tgcagaacgg ct                                                              12

<210> SEQ ID NO 22
<211> LENGTH: 12
<212> TYPE: DNA
<213> ORGANISM: Artificial Sequence
<220> FEATURE:
<223> OTHER INFORMATION: Sequence of the 5' end of the C-ORF product of
      mda-9

<400> SEQUENCE: 22
ggcggcggcg gc                                                              12

<210> SEQ ID NO 23
<211> LENGTH: 12
<212> TYPE: DNA
<213> ORGANISM: Artificial Sequence
<220> FEATURE:
<223> OTHER INFORMATION: Sequence of the 5' end of the C-ORF product of
      PCTA-1A

<400> SEQUENCE: 23
tggaggcctg ga                                                              12

<210> SEQ ID NO 24
<211> LENGTH: 12
<212> TYPE: DNA
<213> ORGANISM: Artificial Sequence
<220> FEATURE:
<223> OTHER INFORMATION: Sequence of the 5' end of the C-ORF product of
      PCTA-1B

<400> SEQUENCE: 24
gccagtgcct ca                                                              12

<210> SEQ ID NO 25
<211> LENGTH: 12
<212> TYPE: DNA
<213> ORGANISM: Artificial Sequence
<220> FEATURE:
<223> OTHER INFORMATION: Sequence of the 5' end of the C-ORF product of
      PCTA-1C

<400> SEQUENCE: 25
cgatgtggcc tt                                                              12

<210> SEQ ID NO 26
<211> LENGTH: 12
<212> TYPE: DNA
<213> ORGANISM: Artificial Sequence
<220> FEATURE:
<223> OTHER INFORMATION: Sequence of the 5' end of the C-ORF product of
      OLD-35

<400> SEQUENCE: 26
cggaggacca at                                                              12
```

<210> SEQ ID NO 27
<211> LENGTH: 12
<212> TYPE: DNA
<213> ORGANISM: Artificial Sequence
<220> FEATURE:
<223> OTHER INFORMATION: Sequence of the 5' end of the C-ORF product of PEGen 12

<400> SEQUENCE: 27
gcggtggtga cg                                                          12

<210> SEQ ID NO 28
<211> LENGTH: 12
<212> TYPE: DNA
<213> ORGANISM: Artificial Sequence
<220> FEATURE:
<223> OTHER INFORMATION: Sequence of the 5' end of the C-ORF product of PEGen 28

<400> SEQUENCE: 28
gtgtggtgtg tc                                                          12

<210> SEQ ID NO 29
<211> LENGTH: 12
<212> TYPE: DNA
<213> ORGANISM: Artificial Sequence
<220> FEATURE:
<223> OTHER INFORMATION: Sequence of the 5' end of the C-ORF product of PEGen 42

<400> SEQUENCE: 29
ggcgttgcga cg                                                          12

<210> SEQ ID NO 30
<211> LENGTH: 60
<212> TYPE: DNA
<213> ORGANISM: artificial sequence
<220> FEATURE:
<223> OTHER INFORMATION: Synthetic oligonucleotide primer D-SLAP
<220> FEATURE:
<221> NAME/KEY: misc_feature
<222> LOCATION: (1)...(60)
<223> OTHER INFORMATION: n = A,T,C or G

<400> SEQUENCE: 30
nnnnnnnnnn nncagagctc aaatttgtga tcagctggtc tttcacaaat ttgagctctg       60

<210> SEQ ID NO 31
<211> LENGTH: 70
<212> TYPE: DNA
<213> ORGANISM: artificial sequence
<220> FEATURE:
<223> OTHER INFORMATION: Synthetic oligonucleotide primer D-CLAP1
<220> FEATURE:
<221> NAME/KEY: misc_feature
<222> LOCATION: (1)...(70)
<223> OTHER INFORMATION: n = A,T,C or G

<400> SEQUENCE: 31
nnnnnnnnnn gggagagctc acagctgaag cagctgacta gcacctagtg tagaatacat       60
cttgagctat                                                             70

<210> SEQ ID NO 32
<211> LENGTH: 70
<212> TYPE: DNA
<213> ORGANISM: artificial sequence
<220> FEATURE:
<223> OTHER INFORMATION: Synthetic oligonucleotide primer D-CLAP2

```
-continued

<220> FEATURE:
<221> NAME/KEY: misc_feature
<222> LOCATION: (1)...(70)
<223> OTHER INFORMATION: n = A,T,C or G

<400> SEQUENCE: 32
nnnnnnnnnn nnnagagctc acagctgaag cagctgacta gcacctagtg tagaatacat      60
cttgagctat                                                             70

<210> SEQ ID NO 33
<211> LENGTH: 60
<212> TYPE: DNA
<213> ORGANISM: artificial sequence
<220> FEATURE:
<223> OTHER INFORMATION: Synthetic oligonucleotide primer T-SLAP

<400> SEQUENCE: 33 ttttttttt ttcagagctc aaatttgtga tcagctggtc tttcacaaat ttgagctctg       60
```